(12) United States Patent
McMahon et al.

(10) Patent No.: US 6,174,291 B1
(45) Date of Patent: Jan. 16, 2001

(54) OPTICAL BIOPSY SYSTEM AND METHODS FOR TISSUE DIAGNOSIS

(75) Inventors: Brain T. McMahon, Minnetonka; Chester E. Sievert, Jr., Mahtomedi; Scott R. Wilson, Maple Grove; Ronald R. Zimmermann, Robbinsdale; Robert A. Palme, Taylor Falls; John G. Yager, Bloomington, all of MN (US); David R. Walsh, River Falls, WI (US)

(73) Assignee: SpectraScience, Inc., Plymouth, MN (US)

(*) Notice: Under 35 U.S.C. 154(b), the term of this patent shall be extended for 0 days.

(21) Appl. No.: 09/037,722

(22) Filed: Mar. 9, 1998

(51) Int. Cl.[7] ................................. A61B 10/00
(52) U.S. Cl. ............................................. 600/564
(58) Field of Search .................... 600/166, 111, 600/176, 564, 113, 129, 130, 187

(56) References Cited

U.S. PATENT DOCUMENTS

| | | | |
|---|---|---|---|
| 4,421,106 | 12/1983 | Uehara | 128/4 |
| 4,479,499 | 10/1984 | Alfano et al. | 128/665 |
| 4,556,057 | 12/1985 | Hiruma et al. | 128/303.1 |
| 4,651,201 * | 3/1987 | Schoolman | 358/98 |
| 4,675,529 * | 6/1987 | Kushida | 250/458.1 |
| 4,718,417 | 1/1988 | Kittrell et al. | |
| 4,755,684 | 7/1988 | Leiner et al. | 250/461.1 |
| 4,895,156 | 1/1990 | Schulze | 128/634 |
| 4,957,114 | 9/1990 | Zeng et al. | 128/665 |
| 4,972,331 | 11/1990 | Chance | 364/550 |

(List continued on next page.)

FOREIGN PATENT DOCUMENTS

| | | | |
|---|---|---|---|
| 19533856 * | 3/1997 | (DE) | A61B/19/00 |
| 0512965 * | 11/1992 | (EP) | |
| WO 83/03189 | 9/1983 | (WO) | |
| WO 94/12095 | 6/1994 | (WO) | |
| WO97/32182 * | 9/1997 | (WO) | |
| WO97/41777 * | 11/1997 | (WO) | |

OTHER PUBLICATIONS

Cothren, R.M., et al., "Detection of dysplasia at colonoscopy using laser–induced fluorescence: a blinded study", *Gastrointestinal Endoscopy*, vol. 44, No. 2, pp. 168–176, (1996).

Kato, H., et al., "Application of Simple Imaging Technique for Fluoresence Bronchoscope: Preliminary Report", *Diagnostic and Therapeutic Endoscopy*, vol. 1, pp. 79–81, (1994).

Schomacker, K.T., et al., "Ultraviolet Laser–Induced Fluroescence of Colonic Tissue: Basic Biology and Diagnostic Potential", *Lasers in Surgery and Medice*, pp. 63–78, (1992).

* cited by examiner

Primary Examiner—Max Hindenburg
Assistant Examiner—Pamela S Wingwood
(74) Attorney, Agent, or Firm—Schwegman, Lundberg, Woessner & Kluth, P.A.

(57) ABSTRACT

A system characterizes tissue using fluorescence spectroscopy, such as light-induced fluorescence. Native fluorescence ("autofluorescence") from endogenous tissue without requiring fluorescence-enhancing agents is used to distinguish between normal tissue, hyperplastic tissue, adenomatous tissue, and adenocarcinomas. The system provides endoscopic image enhancement for easy location of a tissue site for optical biopsy tissue characterization. The system allows the use of an integrated endoscopic diagnosis and treatment device for immediate diagnosis and treatment without interchanging equipment and relocating the tissue site. The system is also integrated with existing endoscopy equipment for initiating and displaying the diagnosis. The system provides an adjunctive tool to histopathological tissue classification or, alternatively, further treatment is based on the optical biopsy system diagnosis itself.

45 Claims, 11 Drawing Sheets

U.S. PATENT DOCUMENTS

| | | | |
|---|---|---|---|
| 5,199,431 | 4/1993 | Kittrell et al. | 128/634 |
| 5,201,318 | 4/1993 | Rava et al. | 128/665 |
| 5,261,410 | 11/1993 | Alfano et al. | 128/664 |
| 5,293,872 * | 3/1994 | Alfono et al. | 600/437 |
| 5,303,026 | 4/1994 | Strobl et al. | 356/318 |
| 5,304,173 | 4/1994 | Kittrell et al. | 606/15 |
| 5,318,023 | 6/1994 | Vari et al. | 128/633 |
| 5,318,024 | 6/1994 | Kittrell et al. | 128/634 |
| 5,321,501 | 6/1994 | Swanson et al. | 356/345 |
| 5,345,941 | 9/1994 | Rava et al. | 128/665 |
| 5,348,018 | 9/1994 | Alfano et al. | 128/665 |
| 4,981,138 | 1/1991 | Deckelbaum et al. | 128/665 |
| 5,042,494 | 8/1991 | Alfano | 128/65 |
| 5,062,428 | 11/1991 | Chance | 128/664 |
| 5,104,392 | 4/1992 | Kittrell et al. | . |
| 5,106,387 | 4/1992 | Kittrell et al. | . |
| 5,115,137 | 5/1992 | Andersson-Engels et al. | 250/461.2 |
| 5,122,974 | 6/1992 | Chance | 364/550 |
| 5,125,404 | 6/1992 | Kittrell et al. | 128/634 |
| 5,131,398 | 7/1992 | Alfano et al. | 128/665 |
| 5,168,162 | 12/1992 | Oong et al. | 250/339 |
| 5,174,297 | 12/1992 | Daikuzono | 128/665 |
| 5,187,672 | 2/1993 | Chance et al. | 364/550 |
| 5,196,709 | 3/1993 | Berndt et al. | 250/458.1 |
| 5,349,961 | 9/1994 | Stoddart et al. | 128/665 |
| 5,349,964 | 9/1994 | Tiemann et al. | 128/634 |
| 5,350,375 | 9/1994 | Deckelbaum et al. | 606/7 |
| 5,353,799 | 10/1994 | Chance | 128/664 |
| 5,369,496 | 11/1994 | Alfano et al. | 356/446 |
| 5,377,676 | 1/1995 | Vari et al. | 128/634 |
| 5,383,467 | 1/1995 | Auer et al. | 128/664 |
| 5,386,827 | 2/1995 | Chance | 128/633 |
| 5,402,778 | 4/1995 | Chance | 128/633 |
| 5,408,966 | 4/1995 | Salb | 128/633 |
| 5,413,108 | 5/1995 | Alfano | 128/665 |
| 5,419,323 | 5/1995 | Kittrell et al. | 128/653.1 |
| 5,421,337 | 6/1995 | Richards-Kortum et al. | 128/665 |
| 5,421,339 | 6/1995 | Ramanujam et al. | 128/665 |
| 5,431,645 * | 7/1995 | Smith et al. | 606/1 |
| 5,439,000 | 8/1995 | Gunderson et al. | 128/664 |
| 5,459,570 | 10/1995 | Swanson et al. | 356/345 |
| 5,465,147 | 11/1995 | Swanson | 356/345 |
| 5,467,767 | 11/1995 | Alfano et al. | 128/665 |
| 5,474,910 | 12/1995 | Alfano | 435/34 |
| 5,485,530 | 1/1996 | Lakowicz et al. | 382/191 |
| 5,504,337 | 4/1996 | Lakowicz et al. | 250/461.2 |
| 5,507,287 | 4/1996 | Palcic et al. | 128/633 |
| 5,553,614 | 9/1996 | Chance | 128/633 |
| 5,555,885 | 9/1996 | Chance | 128/654 |
| 5,562,100 | 10/1996 | Kittrell et al. | 128/665 |
| 5,579,773 | 12/1996 | Vo-Dinh et al. | 128/665 |
| 5,582,168 | 12/1996 | Samuels et al. | 128/633 |
| 5,590,660 | 1/1997 | MacAulay et al. | 128/664 |
| 5,596,987 | 1/1997 | Chance | 128/633 |
| 5,599,717 | 2/1997 | Vo-Dinh | 436/63 |
| 5,601,087 | 2/1997 | Gunderson et al. | 128/664 |
| 5,612,540 | 3/1997 | Richards-Kortum et al. | 250/461.2 |
| 5,623,932 | 4/1997 | Ramanujam et al. | 128/665 |
| 5,635,402 | 6/1997 | Alfano et al. | 436/63 |
| 5,647,368 | 7/1997 | Zeng | 128/665 |
| 5,650,135 | 7/1997 | Contag et al. | 424/9.1 |
| 5,664,574 | 9/1997 | Chance | 128/664 |
| 5,673,701 | 10/1997 | Chance | 128/664 |
| 5,916,146 * | 6/1999 | Allotta et al. | 600/141 |

OPTICAL BIOPSY SYSTEM AND METHODS FOR TISSUE DIAGNOSIS

CROSS REFERENCE TO RELATED APPLICATIONS

This application is related to the following co-pending, commonly assigned U.S. patent applications: application Ser. No. 08/644,080 entitled "OPTICAL BIOPSY FORCEPS," filed on May 7, 1996, application Ser. No. 08/975,734 entitled "OPTICAL BIOPSY FORCEPS," filed on Nov. 21, 1997, application Ser. No. 09/037,240, entitled "OPTICAL BIOPSY FORCEPS SYSTEM AND METHOD OF DIAGNOSING TISSUE", now U.S. Pat. No. 6,066,102, filed on even date herewith, each of which is assigned to the assignee of the present invention, and the disclosure of each being herein incorporated by reference.

TECHNICAL FIELD OF THE INVENTION

This invention relates generally to in vivo tissue surveillance, characterization, diagnosis, and treatment and particularly, but not by way of limitation, to an endoscopic and/or laparoscopic fluorescence spectroscopy optical biopsy system for diagnosing and facilitating the treatment of tissue.

BACKGROUND OF THE INVENTION

Tissue diagnosis is important in many fields of medicine, including, but not limited to: gastrointestinal, cardiovascular, urological, pulmonary, reproductive, dermatology, surgery, and general medicine. For example, early detection of tissue malignancy is essential to avoid the spread of cancer and associated complications. In the gastrointestinal tract, for example, endoscopic and/or laparoscopic "minimally invasive" techniques can be used to obtain a biopsy that provides a physical sample of a tissue site. The tissue site can be either a flat surface or subsurface mucosal lesion or a raised mucosal lesion (e.g., a polyp). The biopsy can be analyzed in a pathology laboratory using histopathological techniques to determine whether it is cancerous. The tissue may be normal, hyperplastic, adenomatous, or malignant. For example, hyperplastic polyps consist of normal tissue, and are therefore benign. Adenomatous polyps, which are also referred to as dysplastic polyps, consist of abnormal tissue, and are a risk of future malignancy. Adenocarcinomas are malignant polyps that pose an immediate risk of spreading to other areas of the body.

Histopathology, while relatively accurate, requires the physical removal of a tissue sample and its time-consuming analysis in a pathology laboratory. Further treatment of the tissue site based on the results of the histopathological analysis may require a second medical procedure, separate from the original diagnostic procedure that obtained the biopsy. Along with an increased cost and patient discomfort, locating the original biopsy site may be extremely difficult. Moreover, gathering a physical biopsy sample is not without risk, since it typically involves cutting and removing a small portion of tissue. For this reason, taking unnecessary physical biopsy samples should be avoided. Sampled tissue sites that are subsequently found to be hyperplastic by histopathological analysis were, in retrospect, unnecessarily sampled.

Moreover, some patients undergoing endoscopic colonic examination, for example, will have an abundance of small (e.g., less than 5 millimeters in diameter) polyps that are either hyperplastic or adenomatous. Since sampling each site is difficult and increases the risk of other complications, physical samples are obtained from only a "representative" subpopulation of the sites. However, this leaves other possibly premalignant sites undiagnosed, even though such sites could become malignant and contribute to the spread of cancer in the patient. Thus, the risk of obtaining physical biopsy samples is compounded when only a subpopulation of the sites is sampled.

In deciding whether to remove a physical biopsy sample for histopathological analysis, an endoscopist typically subjectively determines visually whether a polyp is hyperplastic or adenomatous. The accuracy of existing biopsy methods depends upon the endoscopist's ability to subjectively determine healthy from suspicious tissue to biopsy. However, it is difficult, if not impossible, to visually differentiate between small hyperplastic and small adenomatous polyps, particularly when viewed through the viewing optics of an endoscope. Moreover, because conditions other than cancer can cause tissue discoloration, an accurate visual characterization is extremely difficult, and histopathological analysis of a physical tissue sample is often required. As a result, the subjective visual inspection may leave adenomatous polyps undiagnosed and therefore untreated.

Various tissue classification techniques have also been developed as alternatives or adjuncts to physical biopsy sampling and visual differentiation between tissue characteristics. One class of such techniques involves illuminating tissue with incident light, and allowing the incident light energy to interact with the tissue. The tissue is classified based on light that is returned from the tissue. A particularly interesting class of such techniques, referred to as fluorescence spectroscopy, is based on the observation that different tissue characteristics result in a different fluorescence in the returned light. More particularly, spectral characteristics of the fluorescence returned from premalignant or malignant tissue may be different from that returned from normal or benign tissue.

Many such fluorescence-based techniques depend on the use of extrinsic fluorescence-enhancing dyes, stains, or other image contrast agents. Contrast agents are typically substances that are ingested by the patient, delivered intravenously, or delivered locally to a tissue site to enhance its fluorescence. A contrast agent is known to substantially target only the particular type of tissue being detected, and to increase the fluorescence properties of that type of tissue for obtaining a better image. Contrast agents pose at least two problems. First, their selectivity is less than optimal. Tissue uptake and concentration levels may be significantly variable. The contrast agent attaches to other types of tissue as well as the targeted tissue. This hinders an accurate diagnosis based on observation of returned fluorescence. Second, certain contrast agents have undesirable side-effects, such as acute and/or chronic light-sensitivity of the patient. Thus, fluorescence techniques using extrinsic fluorescence-enhancing agents for diagnosis have limited usefulness.

Other techniques avoid the use of extrinsic fluorescence-enhancing agents, depending instead on native fluorescence (also referred to as autofluorescence) from endogenous tissue. Even without contrast agents, the spectral characteristics of the fluorescence returned from premalignant or malignant tissue may be different from that returned from normal or benign tissue. Such differences, however, are much less pronounced in the absence of extrinsic image contrast agents. Detecting small differences between spectral fluorescence characteristics of different tissue types is much more difficult without using extrinsic image contrast agents. As a result, such systems require complicated and expensive components, such as multiple optical fibers for illuminating or collecting returned fluorescence from the tissue, or image intensification or photomultiplication devices for obtaining an adequate signal from the returned fluorescence.

Other systems do not provide the physician with an actual diagnosis based on tissue classification using fluorescence data. For example, Palcic et al., U.S. Pat. No. 5,507,287 entitled "ENDOSCOPIC IMAGING SYSTEM FOR DISEASED TISSUE," produces a pseudo-color image of the tissue based on the returned fluorescence from the tissue. However, the attending physician must still try to subjectively diagnose the tissue based on the pseudo-image provided on the display.

Even if tissue is accurately diagnosed, by the physician, or otherwise, using endoscopic techniques, treating tissue diagnosed as abnormal is still difficult. Many systems require an exchange of diagnostic and treatment devices. For example, in systems using multiple optical fibers extending through the working channel of an endoscope to diagnose the tissue, the diagnosing optics are removed from the working channel of an endoscope so that a forceps, snare, or ablation device can be extended through the working channel of an endoscope to treat the tissue. However, exchanging diagnostic and treatment devices poses problems. In the colon, for example, inherent colonic motility makes it difficult for the physician to accurately maintain the position of the endoscope during the exchange of diagnosing and treatment devices. As a result, the physician may not be able to locate the previously diagnosed polyp or may inadvertently treat the wrong polyp. Thus, exchanging diagnosing and treatment devices reduces the efficacy of the medical procedure.

In summary, there is a critical medical need for accurate and early diagnosis and treatment of premalignant and malignant tissue to prevent the spread of cancer. Risks and other disadvantages with obtaining physical biopsy samples for histopathological analysis indicate a need for improved techniques for classifying tissue. There is a need for providing accurate diagnosis and immediate treatment of premalignant and malignant tissue, without requiring multiple medical procedures, without using extrinsic agents for enhancing fluorescence, and without using complicated and expensive components in the absence of such contrast agents.

SUMMARY OF THE INVENTION

The present invention provides, among other things, systems, devices, and methods for accurate tissue characterization, without requiring the use of extrinsic fluorescence enhancing agents, and immediate treatment of the tissue based on the tissue characterization. In one embodiment, the invention includes a method. An endoscope having viewing optics and a conduit (such as a "working channel" of the endoscope) is introduced into a living organism. A diagnostic optical fiber is introduced through the conduit into proximity with tissue at a distal end of the endoscope. Excitation electromagnetic energy is transmitted through the diagnostic optical fiber to the tissue without requiring fluorescence-enhancing agents. Electromagnetic energy is received through the diagnostic optical fiber from the tissue in response to the excitation electromagnetic energy. A diagnosis of the tissue is provided using an analysis of a signal that is based on the received electromagnetic energy. The tissue is treated, if indicated by the diagnosis, while the diagnostic optical fiber is still in the conduit of the endoscope. Treating the tissue consists essentially of at least one of the following: taking a physical biopsy sample of at least a portion of the tissue, mechanically removing at least a portion of the tissue, performing electrosurgery on at least a portion of the tissue, delivering a drug or other chemical agent to at least a portion of the tissue, and providing photodynamic therapy to at least a portion of the tissue.

In one embodiment, transmitting excitation electromagnetic energy includes activating a light source using a switch that is located on the endoscope. In another embodiment, the light source is voice-actuated. In another embodiment, providing a diagnosis of the tissue includes forming an intensity spectrum of the received electromagnetic energy. A diagnosis probability is computed based on intensities at particular wavelengths in the intensity spectrum. The diagnosis probability is compared to a threshold probability to characterize the tissue. In a further embodiment, comparing the diagnosis probability to a threshold probability includes basing at least one of the diagnosis probability and the threshold probability on a logistics regression analysis, multivariate linear regression analysis (MVLR), stepwise regression analysis, best subset analysis, spectral peaks(s) ratio analysis, neural network analysis, or other analysis of data obtained from other tissue samples.

In one embodiment, providing the diagnosis of the tissue includes forming the diagnosis based on a slope of the intensity spectrum at particular wavelengths In a further embodiment, providing the diagnosis of the tissue includes forming the diagnosis based on a curvature of the intensity spectrum at particular wavelengths.

In one embodiment, the method includes normalizing the intensity spectrum to a reference intensity spectrum by dividing each intensity at a particular wavelength in the intensity spectrum by an intensity at the corresponding wavelength in the reference intensity spectrum. Alternatively, the intensity spectrum is normalized by dividing each intensity at a particular wavelength in the intensity spectrum by a sum of intensities over a range of wavelengths in the intensity spectrum.

In one embodiment, the intensity spectrum is corrected by subtracting a background reading. In a further embodiment, subtracting a background reading includes correcting for endoscope light.

In one embodiment, providing a diagnosis of the tissue includes forming a probability factor P according to the equation $P = e^s/(1+e^s)$, wherein:

$$s = C + \sum_{i=1}^{n} B_i \cdot I_i$$

and C is a constant, I is a detected return fluorescence intensity at a particular wavelength, B is a constant corresponding to the particular wavelength, and n is any positive integer. The probability factor P is compared to a predetermined value to diagnose the tissue. In one embodiment, C, B, and P are based on a logistics regression analysis of data obtained from other tissue samples.

In another embodiment, providing a diagnosis of the tissue includes forming a score S, wherein:

$$s = C + \sum_{i=1}^{n} B_i \cdot I_i$$

and C is a constant, I is a detected return fluorescence intensity at a particular wavelength, B is a constant corresponding to the particular wavelength, and n is any positive integer. The score S is compared to a predetermined threshold value to diagnose the tissue. In one embodiment, at least one of C, B, and the predetermined threshold value are based on at least one of: logistics regression analysis, multivariate linear regression (MVLR) analysis, stepwise regression analysis, best subset analysis, spectral peak(s) ratio analysis, and neural network analysis.

In another embodiment, providing a diagnosis of the tissue includes forming a score X, wherein:

$$X = \sum_{i=1}^{n} C_i \cdot S_i$$

and C is a constant corresponding to the particular wavelength, S is a slope of the detected return fluorescence intensity spectrum at a particular wavelength, and n is any positive integer. The score X is compared to a predetermined threshold value to diagnose the tissue. In one embodiment, at least one of C and the predetermined threshold value are based on at least one of: logistics regression analysis, multivariate linear regression (MVLR) analysis, stepwise regression analysis, best subset analysis, spectral peak(s) ratio analysis, and neural network analysis.

In another embodiment, providing a diagnosis of the tissue includes forming a score X, wherein:

$$X = \sum_{i=1}^{m} C_i \cdot S_i + \sum_{j=1}^{n} C_j \cdot I_j$$

and C is a constant corresponding to the particular wavelength, S is a slope of the detected return fluorescence intensity spectrum at a particular wavelength, I is an intensity of the detected return fluorescence at a particular wavelength, and m and n are positive integers. The score X is compared to a predetermined threshold value to diagnose the tissue.

In another embodiment, one of the above-described tissue diagnosis techniques is used in combination with another tissue diagnosis technique, such as at least one of: optical coherent tomography, interferometry, optical-acoustic imaging, acoustic-optical imaging, fluorescence imaging, photomigration, time-resolved fluorescence spectroscopy, frequency-domain fluorescence spectroscopy, elastic scattering, Rayleigh scattering, Raman scattering, and other linear or nonlinear optical techniques.

In another embodiment, the method includes providing an audible or visual indicator of the diagnosis such as, for example, displaying an intensity vs. wavelength graph or one or more icons or other audible or visual indicators of whether the characterized tissue should be further treated. According to one aspect of the invention, the indicator overlays a visual image of the tissue displayed on an endoscope monitor.

In another embodiment, the method includes correcting the signal that is based on the received electromagnetic excitation energy by subtracting a background reading. For example, subtracting the background reading includes, among other things, correcting for endoscope light.

Another aspect of the invention provides, among other things, a second method. The method includes introducing into a living organism an endoscope having viewing optics and a conduit. A view at the distal end of the endoscope is displayed on an endoscope monitor. A diagnostic optical fiber is introduced through the conduit into proximity with tissue at the distal end of the endoscope. Electromagnetic excitation energy is transmitted through the diagnostic optical fiber to the tissue. Electromagnetic energy is received through the diagnostic optical fiber from the tissue in response to the excitation electromagnetic energy. A diagnosis of the tissue is provided. The diagnosis is based on an analysis of the received electromagnetic energy. An indicator of the diagnosis is displayed on the endoscope monitor. In one embodiment, displaying an indicator of the diagnosis includes displaying the indicator together with a visual image of the tissue displayed on the endoscope monitor.

Another aspect of the invention provides, among other things, a third method. An endoscope, including viewing optics and a conduit, is introduced into a living organism. A diagnostic optical fiber is introduced through the conduit into proximity with tissue at a distal end of the endoscope. A video image of the tissue is obtained and digitally enhanced. A tissue site is located based on the enhanced video image of the tissue. Excitation electromagnetic energy is transmitted through the diagnostic optical fiber to the located tissue site without requiring fluorescence-enhancing agents. Electromagnetic energy is received through the diagnostic optical fiber from the tissue site in response to the excitation electromagnetic energy. A diagnosis of the tissue site is provided using an analysis of a signal that is based on the received electromagnetic energy. The tissue site is treated, if indicated by the diagnosis, while the diagnostic optical fiber is still in the conduit of the endoscope. Treating the tissue site consists essentially of at least one of the following: taking a physical biopsy sample of at least a portion of the tissue site, mechanically removing at least a portion of the tissue site, performing electrosurgery on at least a portion of the tissue site, delivering a drug or other chemical agent to at least a portion of the tissue site, and providing photodynamic therapy to at least a portion of the tissue.

Another aspect of the invention provides, among other things, a fourth method. An endoscope having viewing optics and a working channel conduit is introduced into a patient's colon, for example. A diagnostic optical fiber and coaxially integrated forceps is introduced through the conduit into proximity with tissue at a distal end of the endoscope. Excitation light pulses are generated. The excitation light pulses are coupled to the diagnostic optical fiber using a dichroic mirror. The excitation light pulses are transmitted through the diagnostic fiber to the tissue without requiring fluorescence-enhancing agents. Return light is received through the diagnostic optical fiber from the tissue in response to the excitation light pulses. The return light is filtered to obtain a return fluorescence light by removing components of the return light having a wavelength that is approximately shorter than approximately 355 nanometers. The filtered return light is spatially separated to obtain a return fluorescence spectrum. The intensity of the return fluorescence spectrum is detected at a plurality of wavelengths. The detected return fluorescence intensity spectrum is corrected by subtracting a background reading. The tissue is then characterized. Tissue characterization includes forming a probability factor P according to the equation $P = e^S / (1 + e^S)$, wherein:

$$s = C + \sum_{i=1}^{n} B_i \cdot I_i$$

and C is a constant, I is a detected return fluorescence intensity at a particular wavelength, and B is a constant corresponding to the particular wavelength. The probability factor P is compared to a predetermined value to diagnose the tissue. An indicator of the diagnosis is displayed on an endoscope monitor, together with a visual image of the tissue. A physical biopsy sample of the tissue is taken, if indicated by the diagnosis, while the diagnostic optical fiber is still in the working channel conduit of the endoscope.

Another aspect of the invention provides, among other things, an endoscopic system for analyzing, diagnosing, and treating tissue. The system includes an electromagnetic excitation energy source. A single diagnostic optical fiber is adapted to extend through a conduit in an endoscope, from a proximal end of the endoscope to a distal end of the endoscope. The diagnostic optical fiber transmits the electromagnetic excitation energy to a tissue and receiving an electromagnetic response from the tissue at the distal end of the endoscope. A spectrophotometer receives the electromagnetic response and provides a resulting spectral response signal. An optical coupler couples the electromagnetic excitation energy from the energy source to the diagnostic optical fiber, and coupling the electromagnetic response to the spectrophotometer. A diagnosis module receives the spectral response signal and provides a resulting tissue classification without requiring fluorescence-enhancing agents at the tissue. A tissue treatment apparatus is integrally formed with the diagnostic optical fiber. The tissue treatment apparatus is selected from the group consisting essentially of: a biopsy forceps, a biopsy needle, a polyp snare, an radio-frequency (RF) ablation apparatus, an electrosurgical apparatus, a photodynamic therapy (PDT) apparatus, a drug or chemical agent delivery apparatus, a guidewire, and a catheter.

In one embodiment, the optical coupler includes a mirror for reflectively coupling the electromagnetic excitation energy to the diagnostic optical fiber. The optical coupler also includes at least one lens for coupling the electromagnetic response to the spectrophotometer.

In another embodiment, the system also includes an interface circuit. The interface circuit is adapted for displaying an indicator of at least one of the spectral response signal and the tissue classification to an endoscope monitor. In one embodiment, the interface circuit is adapted for receiving a video signal image of the tissue at the distal end of the endoscope, and adapted for providing the video signal image together with an indicator of the tissue classification to an endoscope monitor. In a further embodiment, the interface circuit further comprises an image enhancement module, coupled to the interface circuit, for enhancing the video signal image of the tissue at the distal end of the endoscope.

In one embodiment, the tissue treatment apparatus is coaxially formed with the single diagnosing optical fiber concentrically located at the center of the tissue treatment apparatus. In another embodiment, the electromagnetic excitation energy source is coupled to and actuated by a switch that is located on the endoscope. In a further embodiment, the electromagnetic excitation energy source is voice-actuated.

Another aspect of the invention provides a second system for analyzing, diagnosing, and treating tissue. The system includes a pulsed laser, with or without a wavelength-shifting dye module, providing electromagnetic excitation energy. A single diagnostic optical fiber is adapted to extend through a working channel conduit in an endoscope, from a proximal end of the endoscope to a distal end of the endoscope, for transmitting the electromagnetic excitation energy to and receiving an electromagnetic response from a colonic tissue site at the distal end of the endoscope. The single diagnostic fiber is coaxially and concentrically integrally formed within a treatment apparatus. The tissue treatment apparatus is selected from a group that consists essentially of: a biopsy forceps, a biopsy needle, a polyp snare, an radio-frequency (RF) ablation apparatus, an electrosurgical apparatus, a photodynamic therapy (PDT) apparatus, a drug or chemical agent delivery apparatus, a guidewire, and a catheter. A spectrophotometer receives the electromagnetic response and provides a resulting spectral response signal. The spectrophotometer includes a spectrograph for providing spatial dispersion of the spectral response signal. The spectrophotometer also includes an optical detector for detecting the spatially dispersed spectral response signal. The spectrophotometer further includes a thermoelectric cooler for regulating the temperature of the optical detector. The system further includes an optical coupler, coupling the electromagnetic excitation energy from the pulsed laser to the diagnostic optical fiber, and coupling the electromagnetic response to the spectrophotometer. The optical coupler includes a dichroic mirror for reflectively coupling the electromagnetic excitation energy to the diagnostic optical fiber. The optical coupler also includes at least one lens for coupling the electromagnetic response to the spectrophotometer. The system also includes a diagnosis module. The diagnosis module receives the spectral response signal and provides a resulting tissue classification without requiring fluorescence-enhancing agents at the tissue. The diagnosis module also includes an executable sequence of instructions for classifying the tissue. The system also includes an interface circuit for receiving a video signal image of the tissue at the distal end of the endoscope. The interface circuit is adapted for providing the video signal image together with an indicator of the tissue classification to an endoscope monitor. In one embodiment, the system further includes an image enhancement module, coupled to the interface circuit, for enhancing the video signal image of the tissue at the distal end of the endoscope.

In summary, the present invention provides, among other things, systems, devices and methods for using native fluorescence to characterize tissue without requiring fluorescence-enhancing agents. Image enhancement capability allows easy location of tissue sites to be diagnosed. The system allows the use of a single diagnostic optical fiber that is coaxially integrated with a treatment apparatus. Immediate diagnosis allows immediate treatment, such as by using the integrated diagnostic and treatment apparatus. As a result, treatment does not require removing a diagnostic apparatus, and trying to relocate the tissue site using a treatment apparatus. The present invention also allows easy integration with existing endoscopy equipment, including endoscopes and/or laparoscopes, endoscope monitors, and endoscope computers. Other advantages of the invention will be apparent upon reading the detailed description of the invention below, together with its accompanying drawings.

BRIEF DESCRIPTION OF THE DRAWINGS

In the drawings, like numerals describe substantially similar components throughout the several views.

DETAILED DESCRIPTION OF THE INVENTION

Figure 1A:
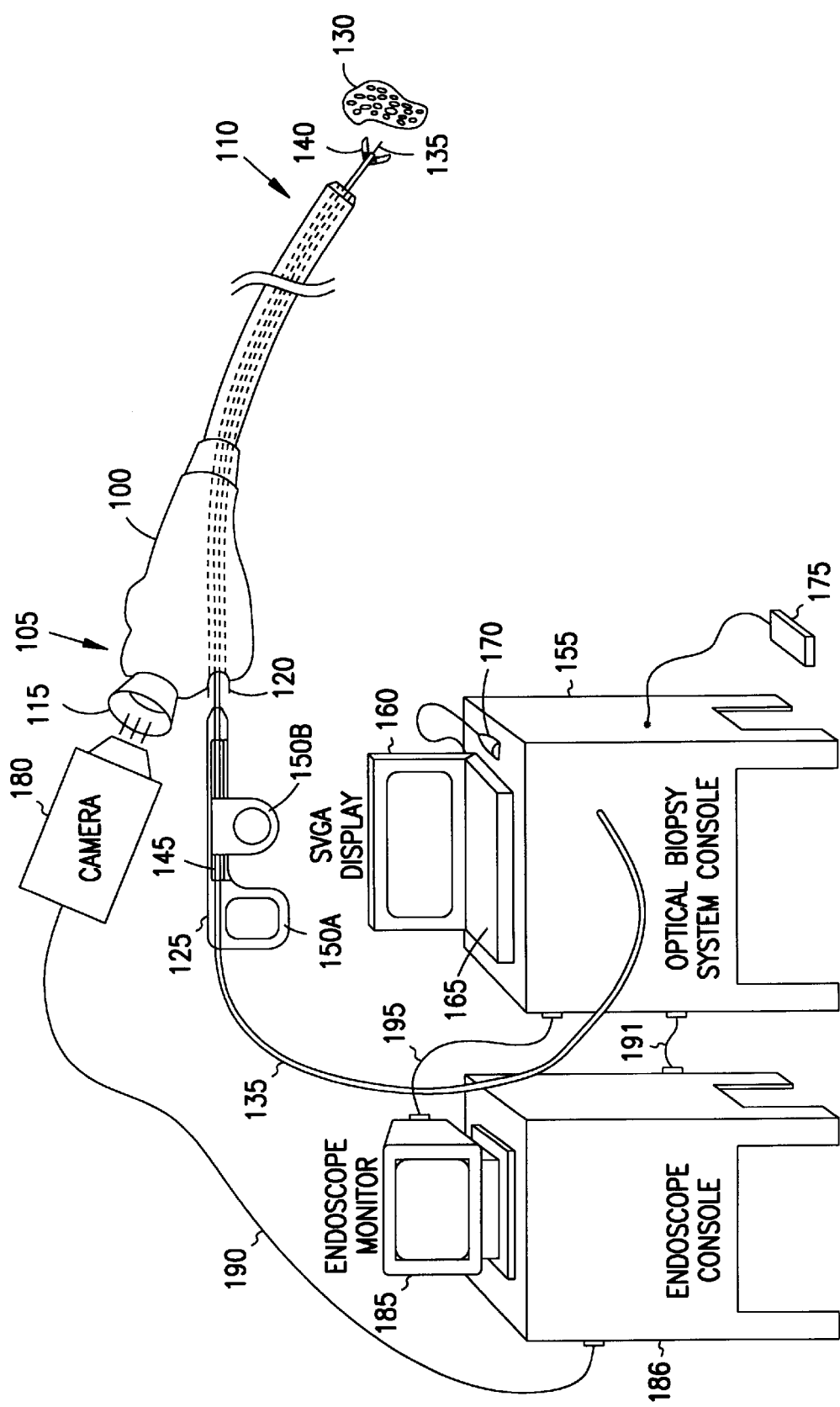
FIG. 1A illustrates generally one embodiment of portions of an endoscopic system for tissue diagnosis and the environment in which it is used.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the scope of the present invention. The precise shapes and sizes of the components described or illustrated are not essential to the invention unless otherwise indicated. The following detailed description is, therefore, not to be taken in a limiting sense, and the scope of the present invention is defined by the appended claims and their equivalents.

Definitions

"Distal" refers to a direction toward an end inserted into the patient. "Proximal" refers to a direction toward an end remaining outside the patient. "Native fluorescence" and "autofluorescence" refer to fluorescence from tissue not treated with dyes, stains, or other image contrast agents used to enhance the fluorescence characteristics of tissue. "Endogenous tissue" refers to tissue not treated with dyes stains, or other image contrast agents, such that its fluorescence characteristics are inherent to the tissue itself. "Endoscope" and "endoscopic" includes generally, but is not limited to, any instrument for examining interior portions of a living organism, including laparoscopic instruments and techniques. "Endoscope" includes a fiberscope, having at least one optical fiber for delivering white light to the tissue and having at least one optical fiber for transmitting a resulting image of the tissue to a camera. "Endoscope" also includes a digital endoscope, having at least one optical fiber for delivering white light to the tissue, and having an optical detector in close proximity with the tissue for receiving a visual image and providing a resulting electrical video signal to a monitor or computer. "Treatment" includes the taking of a physical biopsy sample with a forceps, needle, or other instrument, removal of tissue with a snare or other instrument, ablation and/or electrocautery of the tissue using radio-frequency (RF) energy, delivery of a drug or other chemical agent to the tissue, photodynamic therapy (PDT) including delivering light to activate a drug or chemical agent at or in the tissue, and treatment using a guidewire and catheter. "Biopsy" includes both taking a physical sample, such as for histopathological analysis, or otherwise characterizing or classifying the tissue, such as by using optical or other techniques. "Optical biopsy" includes characterizing or classifying a portion of a living organism by using optical techniques instead of by taking a physical sample. "Spectrograph" includes any device providing, across a spectrum of wavelengths, spatial separation or dispersion of electromagnetic intensities. "Spectrophotometer" includes any instrument that provides a signal indicating a spectral electromagnetic intensity across a range of wavelengths, and may include, as one of its components, a spectrograph.

System Overview

FIG. 1A illustrates generally one embodiment of portions of an endoscopic system for tissue diagnosis using native fluorescence, and the environment in which it is used, according to one aspect of the present invention. FIG. 1A includes an endoscope 100 for examining the interior of a patient's respiratory tract, upper or lower gastrointestinal tract, or urinary tract. Many commercially available endoscopes 100 will be suitable for use according to the present invention. Endoscope 100 includes a proximal end 105, a distal end 110, and viewing optics 115. Viewing optics 115 includes an optical fiber extending through endoscope 100 for providing illumination at distal end 110. Viewing optics 115 also includes, in one embodiment, an optical fiber extending through endoscope 100 for viewing, at proximal end 105, the image at distal end 110. In another embodiment, viewing optics 115 includes an optical detector at distal end 110 of endoscope 100, providing an electrical video signal that is communicated to the proximal end 105 of endoscope 100. Working channel 120 provides a conduit between proximal end 105 and distal end 110 through which various endoscopic accessories can be inserted.

FIG. 1A illustrates, by way of example, but not by way of limitation, one such endoscopic accessory, an integrated diagnosis and treatment device 125, extending through working channel 120 of endoscope 100 for classifying and treating tissue 130. In certain embodiments, device 125 includes an optical biopsy forceps, such as described in one of the following co-pending, commonly assigned U.S. patent applications: application Ser. No. 08/644,080 entitled "OPTICAL BIOPSY FORCEPS," filed on May 7, 1996, application Ser. No. 08/975,734 entitled "OPTICAL BIOPSY FORCEPS," filed on Nov. 21, 1997, application Ser. No. 09/037,240, entitled "OPTICAL BIOPSY FORCEPS WITH ACCESS LUMEN," filed on even date herewith, each of which is assigned to the assignee of the present invention, and the disclosure of each being herein incorporated by reference.

In another embodiment, device 125 includes a photodynamic therapy (PDT) device. The photodynamic therapy device is guided by the fluorescence spectroscopy diagnosis. The photodynamic therapy device delivers light to photoactivate a drug or chemical agent in the tissue, wherein the drug is either previously administered to the patient, or is locally delivered by the photodynamic therapy device itself. In other embodiments, device 125 includes, by way of example, but not by way of limitation a polyp snare, a radio-frequency (RF) ablation apparatus, an electrosurgery apparatus, a drug or chemical agent delivery apparatus, and a guidewire and catheter. Examples of guidewires and catheters are described in Gunderson et al. U.S. Pat. No. 5,601,087 entitled "SYSTEM FOR DIAGNOSING TISSUE WITH GUIDEWIRE," Gunderson et al. U.S. Pat. No. 5,439,000 entitled "METHOD OF DIAGNOSING TISSUE WITH GUIDEWIRE," and Auer et al. U.S. Pat. No. 5,383,467 entitled "GUIDEWIRE CATHETER AND APPARATUS FOR DIAGNOSTIC IMAGING," each of which is assigned to the assignee of the present invention, and each of which is incorporated herein by reference.

The optical biopsy forceps includes a diagnosing optical fiber 135 for contacting tissue 130 at distal end 110 of endoscope 100. The optical biopsy forceps also includes an integrated tissue treatment device, such as forceps 140. Using forceps 140, a physical biopsy sample of tissue 130 is taken if indicated by the diagnosis of tissue 130. In one embodiment, forceps 140 is operatively controlled by wires extending through working channel 120 and coupled to portions of handle 145 near the proximal end 105 of endoscope 100. By manipulating finger pieces 150A–B or other levers on handle 145, opposing jaws of forceps 140 are opened and closed.

Diagnostic optical fiber 135 is coupled to console 155, or any other suitable apparatus for carrying components needed for diagnosing, characterizing, or otherwise classifying tissue 130 using electromagnetic energy. In one embodiment, console 155 also includes high resolution (e.g., 1024×768 pixels) user display 160 and one or more user input devices such as, for example, keyboard 165, mouse 170, and footswitch 175, or switch located on endoscope 100, or microphone for voice-actuation of a diagnostic procedure.

In one embodiment, endoscope 100 further includes camera 180 for displaying a view at the distal end 110 of endoscope 100, obtained through viewing optics 115, on endoscope monitor 185. According to one aspect of the invention, an electrical output signal (also referred to as a video signal) from camera 180 is coupled at node 190 to an endoscope computer in endoscope instrument suite console ("endoscope console") 186. A resulting video output signal from the endoscope computer is coupled to console 155, such as at node 191, before being directly or indirectly coupled at node 195 to endoscope monitor 185. Camera 180 may also be included in the rack-mounted accessory equipment and optically coupled to viewing optics 115 of endoscope 100 through an optical fiber. In one embodiment, console 155 outputs a signal at node 195 to endoscope monitor 185 so that an audible or visual indicator of the tissue diagnosis can be provided (e.g., displayed on endoscope monitor 185 together with the view seen at the distal end 110 of endoscope 100).

Figure 1B:
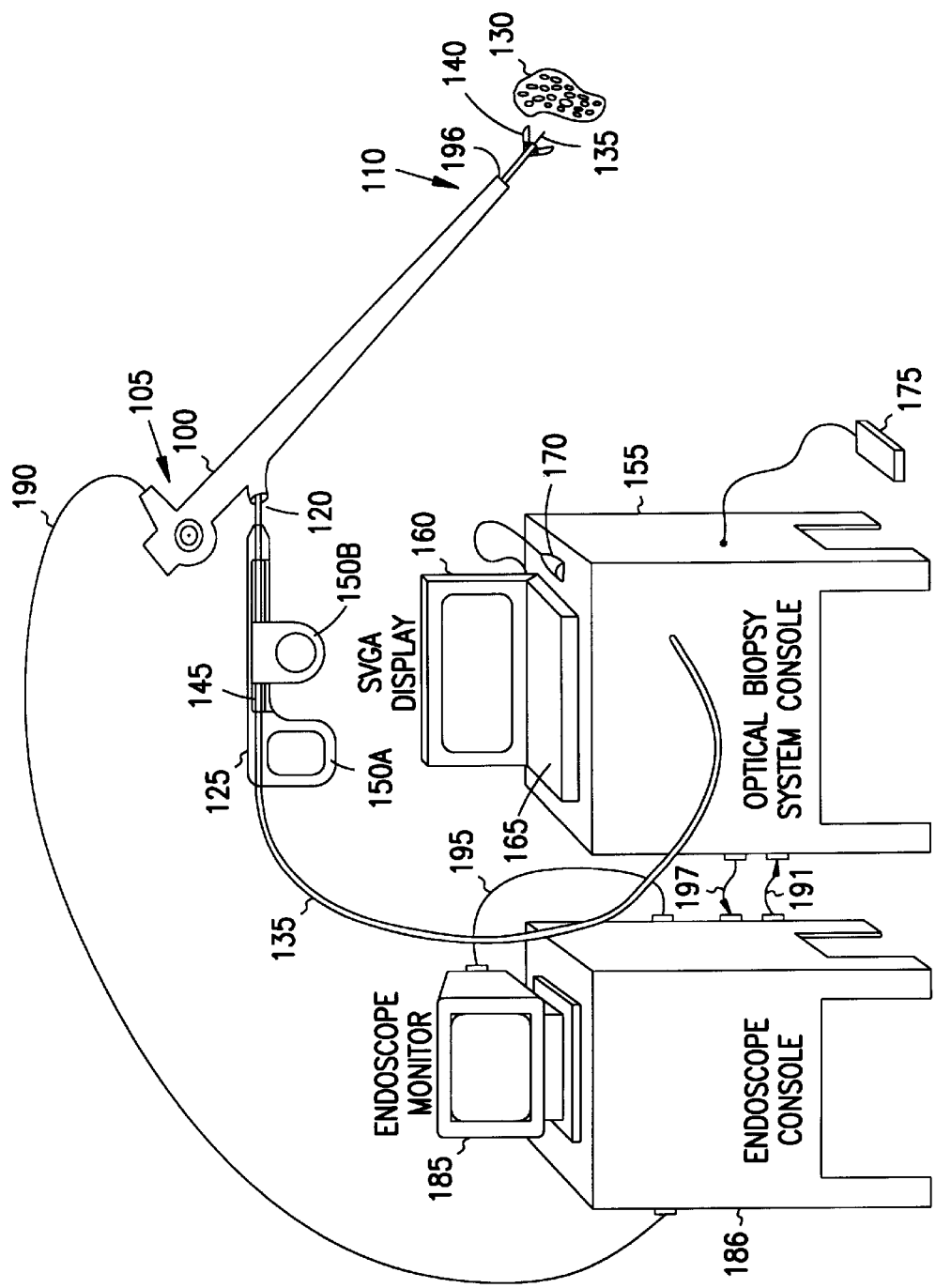
FIG. 1B illustrates generally another embodiment of portions of an endoscopic system for tissue diagnosis and the environment in which it is used.

FIG. 1B illustrates an alternative embodiment of portions of the endoscopic system and its environment. In FIG. 1A, endoscope 100 is an example of a fiberscope, in which an optical signal is communicated from distal end 110 to proximal end 105 of endoscope through viewing optics 115. At proximal end 105, the optical signal is converted into an electrical video signal at node 190 by camera 180. In FIG. 1B, endoscope 100 an example of a digital endoscope 100, in which an image at distal end 110 is acquired by viewing optics that include a charge-coupled device (CCD) imaging integrated circuit (IC) 196, which is located at distal end 110 of endoscope 100. Imaging IC 196 provides an electrical video signal that is communicated from distal end 110 to proximal end 105 of endoscope 100. The video signal is coupled, at node 190, to an endoscope computer in endoscope console 186. A video signal output from the endoscope computer is coupled to console 155 at node 191.

In one embodiment, console 155 overlays an indicator of the tissue characterization on the video signal, so that the video signal contains both the visual image of tissue 130 and the indicator of the tissue diagnosis performed by console 155. This combined video signal is coupled at node 197 through the endoscope computer in endoscope console 186 and, at node 195, to the RGB video input of endoscope monitor 185. Alternatively, the combined video signal is coupled from console 155 directly to the RGB video input of endoscope monitor 185, as illustrated in FIG. 1A.

Optical Configuration Example

Figure 2:
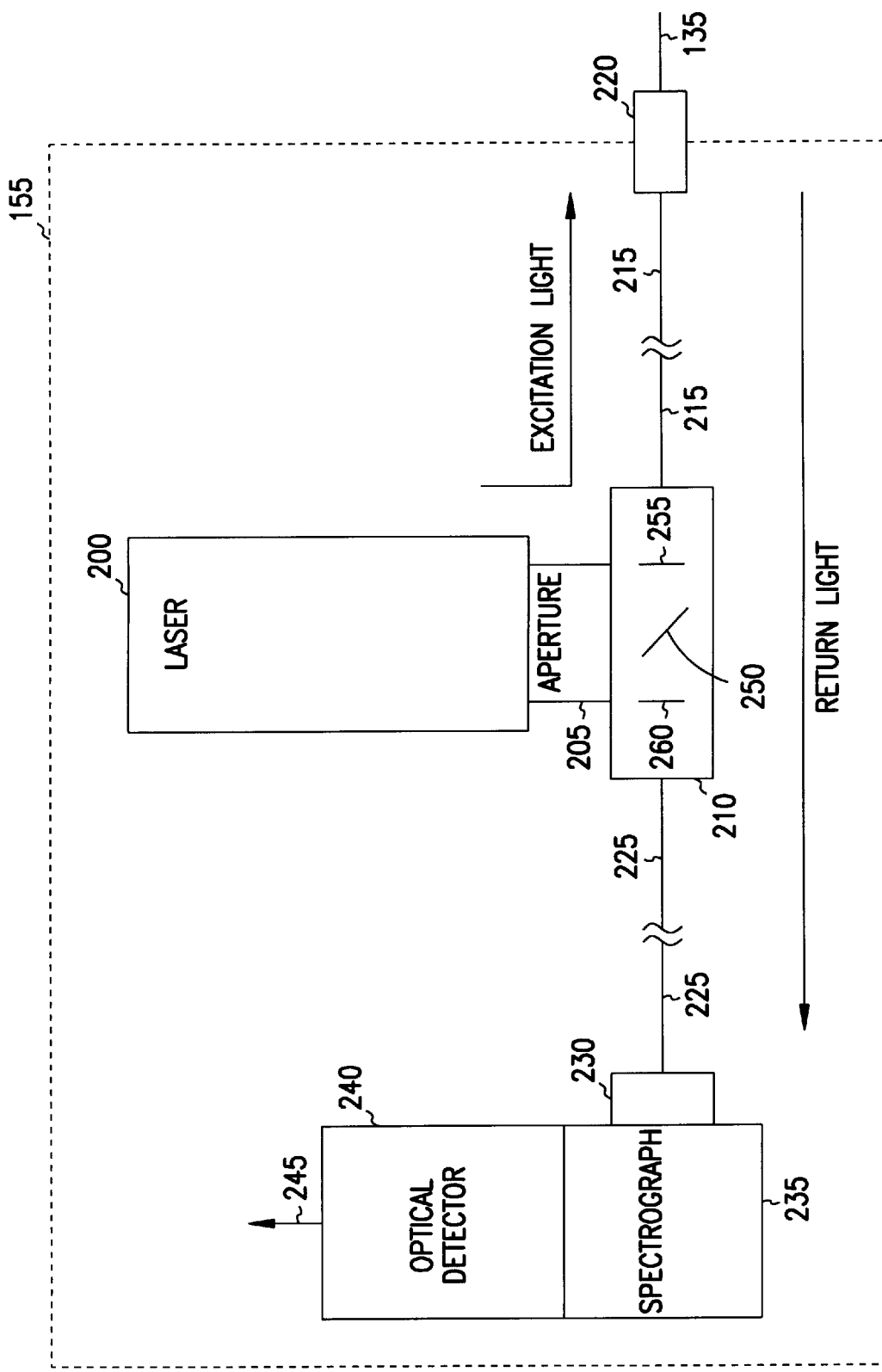
FIG. 2 is a block diagram illustrating generally one embodiment of an optical configuration of portions of the present invention.

FIG. 2 is a block diagram illustrating generally one embodiment of an optical configuration of portions of the present invention. In one embodiment, a coherent light source, such as pulsed or continuous-wave laser 200, provides electromagnetic excitation energy ("excitation light"). In other embodiments, a noncoherent light source is used to provide excitation light, such as, for example, a Xenon flash bulb or an endoscope white light source used for illuminated viewing of tissue at the distal end 110 of endoscope 100. The excitation light is coupled to tissue 130 through aperture 205, optical coupler 210, optical fiber 215, optical coupler 220, and through diagnostic optical fiber 135. In response to the excitation light, return light is received from tissue 130 through diagnostic optical fiber 135, optical coupler 220, optical fiber 215, optical coupler 210, optical fiber 225. A component of this return light includes light-induced fluorescence electromagnetic energy (referred to as "return fluorescence"). The return light also includes other components (e.g., reflected excitation light, and absorbed then scattered excitation light).

The return fluorescence component of the return light is passed through filter 230 to a spectrophotometer, such as spectrograph 235. Spectrograph 235 spatially separates the spectral components of the return fluorescence for detection by optical detector 240. Optical detector 240 provides a resulting electrical data output signal at node 245 for analysis by a tissue characterization and diagnosis module, described below.

Laser 200 provides excitation light having a wavelength that is approximately between 300 nanometers (nm) and 990 nm. In one embodiment, laser 200 includes a pulsed nitrogen laser, with or without a wavelength-shifting dye module. In one embodiment, laser 200 includes a Model 33799-01, or a Model 337ND, each available from Laser Science, Inc. of Franklin, Mass. In this embodiment, laser 200 provides excitation light having a wavelength of approximately 337 nanometers (nm). Laser 200 delivers excitation light at a pulse rate that is approximately between 1 and 20 Hertz (e.g., at approximately 10 Hz). The pulsewidth of the excitation light includes a range that is approximately between 3 nanoseconds (ns) and 10 ns (e.g., 4 ns). In one embodiment, approximately between 1 and 100 pulses (e.g., approximately between 4–10 pulses) are used to perform a single classification of tissue 130. Other wavelengths, pulse rates, pulsewidths, and numbers of pulses could also be used.

In one embodiment, the light output from laser 200 is adjusted by aperture 205, which includes a mechanical aperture/iris that adjusts the beam size (e.g., a beam diameter that is approximately between 0 millimeters (mm) and 9 mm, such as at approximately 2 millimeters) to obtain a desired output power (e.g., approximately 10–60 microjoules, or greater, per pulse, or approximately 30–40 microjoules, or greater, per pulse). From aperture 205, the light output from laser 200 is received by optical coupler 210.

In one embodiment, optical coupler 210 includes mirror 250, lens 255, and lens 260. Mirror 250 is angularly positioned such that light received from laser 200 is reflected toward lens 255 (e.g., at a 90 degree angle). In one embodiment, mirror 250 is a dichroic mirror (also referred to as a beamsplitter) that receives the light output by laser 200, and reflects only wavelengths of approximately 337 nanometers toward lens 255. In one embodiment, dichroic mirror 250 is available from Omega Optical, Inc., of Brattleboro, Ver., and provides approximately 95% reflection for incident light wavelengths less than approximately 350 nm and approximately 90% transmission for incident light wavelengths that exceed approximately 350 nm.

Lens 255 focuses the 337 nm incident light onto optical fiber 215. In one embodiment, lens 255 is a plano-convex synthetic fused silica lens, such as a Model 01 LQP 001, available from Melles Griot of Irvine, Calif. In one embodiment, optical fiber 215 is a multimode optical fiber that is capable of transmitting a broad spectrum of light wavelengths, such as an H Series Optical Fiber available from Meteor Optics, Inc. of Glendale, Ariz. Optical fiber 215 has an optically transmissive (e.g., fused silica) diameter of approximately between 75 and 600 micrometers ($\mu$m) (e.g., 300 $\mu$m), a numerical aperture of NA$\approx$0.22, and is buffered with polyimide, silicone, acrylate, or any other suitable material. Optical fiber 215 is secured to optical coupler 210 by an optical fiber holder. The excitation light that is transmitted through optical fiber 215 is coupled to diagnostic optical fiber 135 by optical coupler 220, such as a Subminiature type A (SMA) 905 interface. Optical coupler 220 provides concentric alignment in its coupling of optical fiber 215 and diagnostic optical fiber 135.

The excitation light is transmitted through diagnostic optical fiber 135 to tissue 130 at distal end 110 of endoscope 100. In response to the excitation light, return light, including a return fluorescence, is received from endogenous tissue 130 without requiring any fluorescence-enhancing agents. The return fluorescence wavelengths (e.g., approximately between 375 nm and 600 nm) exceed the excitation wavelength of 337 nm. The return light is transmitted through diagnostic optical fiber 135, optical coupler 220, and optical fiber 215 to optical coupler 210. In optical coupler 210, the return light is collimated by lens 255. Since the return fluorescence has different wavelengths than those reflected by dichroic mirror 250, the return fluorescence is transmitted through dichroic mirror 250 to lens 260.

Lens 260 focuses the return light onto optical fiber 225, which is secured to optical coupler 210 by an optical fiber holder. In one embodiment, optical fiber 225 is a multimode optical fiber having an optically transmissive fused silica diameter of approximately 400 m. and a polyamide outer cladding. The larger diameter of optical fiber 225 allows for some misalignment with optical coupler 210 (e.g., inaccurate focus by lens 260 due to mechanical shock or vibration) in transmitting return light. In one embodiment, optical coupler 210 includes adjustment knobs for adjusting the position of at least one of optical fibers 225 and 215 in relation to respective lenses 260 and 255, or vice-versa. This ensures that lenses 260 and 255 are focused on the optically transmissive portions of optical fibers 225 and 215, respectively, and minimizes misalignment effects.

Optical fiber 225 transmits the return light to filter 230. In one embodiment, filter 230 is a long pass filter that substantially removes portions of the return light have wavelengths shorter than approximately 355 nm, including the reflected component of the excitation light at a wavelength of approximately 337 nm. The return fluorescence passes through the long pass filter, since its wavelengths exceed the long pass filter cutoff of approximately 355 nm. In one embodiment, long pass filter 230 has a minimum transmission exceeding 90% for wavelengths greater than approximately 360 nm, and a maximum transmission of 0.05% for wavelengths less than approximately 337 nm., and is available from Barr Associates of Westford, Mass.

Spectrograph 235 receives the return fluorescence from filter 230 and spatially separates the spectral components of the return fluorescence for detection by optical detector 240. In one embodiment, spectrograph 235 and optical detector 240 are available together, sold as a Model 77442 spectrograph 235 and an INSTASPEC IV model optical detector 240, each from Oriel Instruments of Stratford, Conn. In this embodiment, optical detector 240 is a 1024×256 pixel charge-coupled device (CCD) array detector. Optical detector 240 is includes a thermoelectric cooler for maintaining its temperature at approximately 0 degrees Celsius to reduce its dark-current noise.

Spectrograph 235 provides a return fluorescence light spectrum that ranges from approximately 275 nm to 725 nm for gastrointestinal polyp detection applications. For other applications, other return fluorescence wavelengths will result. This 275–725 nm spectral range is spread across the 1024 pixel dimension of CCD optical detector 240. Each of the 1024 discrete wavelengths is detected by 256 CCD detector elements. In a fully vertical mode of operation, the data from the 256 CCD detector elements at each of the 1024 discrete wavelengths is summed, providing a resulting 1024 data points corresponding to the 1024 discrete wavelengths. The resulting 1024 data points obtained in response to a light pulse is referred to as a frame of data. A series of light pulses results in a series of data frames that are stored and transferred to a tissue characterization and diagnosis module, as described below. Though spectrograph 235 provides data at wavelengths approximately between 275–725 $\mu$m, much of the return fluorescence data for tissue characterization is typically contained within a range of wavelengths that is approximately between 375 nm and 600 nm, as described below.

Signal Processing and Diagnostics Hardware Example

Figure 3A:
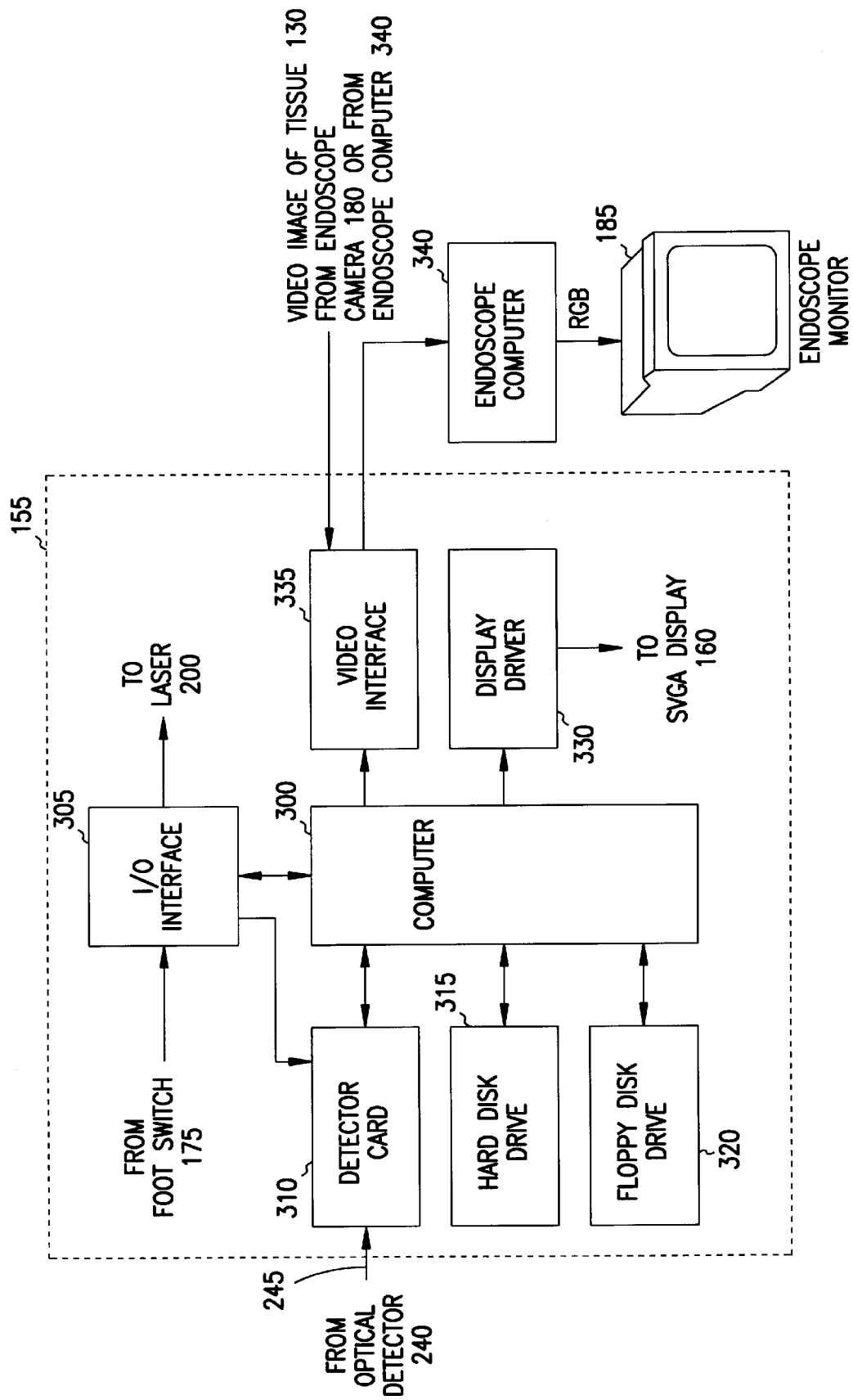
FIG. 3A is a block diagram illustrating generally one embodiment of a hardware configuration for performing signal processing and diagnosis for tissue classification.

FIG. 3A is a block diagram illustrating generally one embodiment of a hardware configuration for performing signal processing and diagnosis for tissue classification. The embodiment of FIG. 3A includes computer 300 and I/O interface 305. In one embodiment, I/O interface 305 is a Model CTM-10 available from Keithley Metrabyte of Cleveland, Ohio. I/O interface 305 receives a user input signal from the operator, such as from footswitch 175, for initiating a tissue diagnosis.

Alternatively, I/O interface 305 initiates tissue diagnosis based on a user input signal received from any other device such as, for example, based on input received from one or more switches located on proximal end 105 of endoscope 100, or is voice-activated using a microphone and a voice-recognition module. In such an embodiment, the present invention provides low-cost integration with existing endoscopy equipment already in use. This also makes the present invention easy for an endoscopist to use.

Tissue diagnosis is initiated by computer 300, which sends a trigger signal, such as a TTL square wave trigger signal, to detector card 310 and laser 200 through I/O interface 305. Detector card 310 receives, at node 245, the return fluorescence spectral signal from optical detector 240. In one embodiment, detector card 310 is available together with optical detector 240, as an INSTASPEC IV model from Oriel Instruments of Stratford, Conn. In response to each light pulse, optical detector 240 serially provides a frame of data having 1024 analog data points, each corresponding to a particular wavelength or range of wavelengths. Detector card 310 performs an 8-bit analog-to-digital (A/D) conversion on each of the 1024 analog data points in the frame of data received from optical detector 240.

In response to each light pulse, detector card 310 provides a resulting 1024 byte output data frame to be stored by computer 300, such as on hard disk drive 315. In one example computer 300 is a single board personal computer including a 166 MHz microprocessor sold as a PENTIUM model by Intel Corp. of Santa Clara, Calif., and using an operating system sold as WINDOWS 95 by Microsoft Corp. of Redmond, Wash. Computer 300 includes a diagnosis module, implemented as a sequence of instructions on the microprocessor, for processing the digitized data received from detector card 310 to provide a tissue characterization or diagnosis, as described below. In one embodiment, computer 300 includes a hard disk drive 315, such as a 2 gigabyte (GB) EIDE hard disk drive. Computer 300 also optionally includes a removable disk, such as floppy disk drive 320, for storing tissue data files and diagnosis information. Display driver 330 provides an indicator of the tissue diagnosis and/or an instantaneous or average intensity vs. wavelength graph of the return fluorescence spectra to display 160.

In one embodiment, the present invention includes a video interface 335 for providing an indicator of the tissue diagnosis to a commercially available endoscope monitor 185, either directly or through a commercially available endoscope computer 340. According to one aspect of the invention, endoscope 100 and accompanying camera 180, endoscope computer 340, and endoscope monitor 185 are existing equipment already available. An endoscopist typically views, on endoscope monitor 185, a visual image of the tissue 130 at the distal end 110 of the endoscope 100. Video interface 335 of the present invention advantageously provides an indicator of the tissue diagnosis to the same endoscope monitor 185 together with the visual image of the tissue 130 obtained from camera 180. In one embodiment, for example, video interface 335 includes a CORONA model video overlay board available from Matrox of Quebec, Canada, such as for overlaying an indicator of the tissue diagnosis on the video image of the tissue 130 displayed on endoscope monitor 185. As a result, the present invention provides low-cost integration with existing endoscopy equipment already in use. This also makes the present invention easy for an endoscopist to use, and easy to integrate into the existing medical routine procedures.

Hardware Example Including Image Enhancement

Figure 3B:
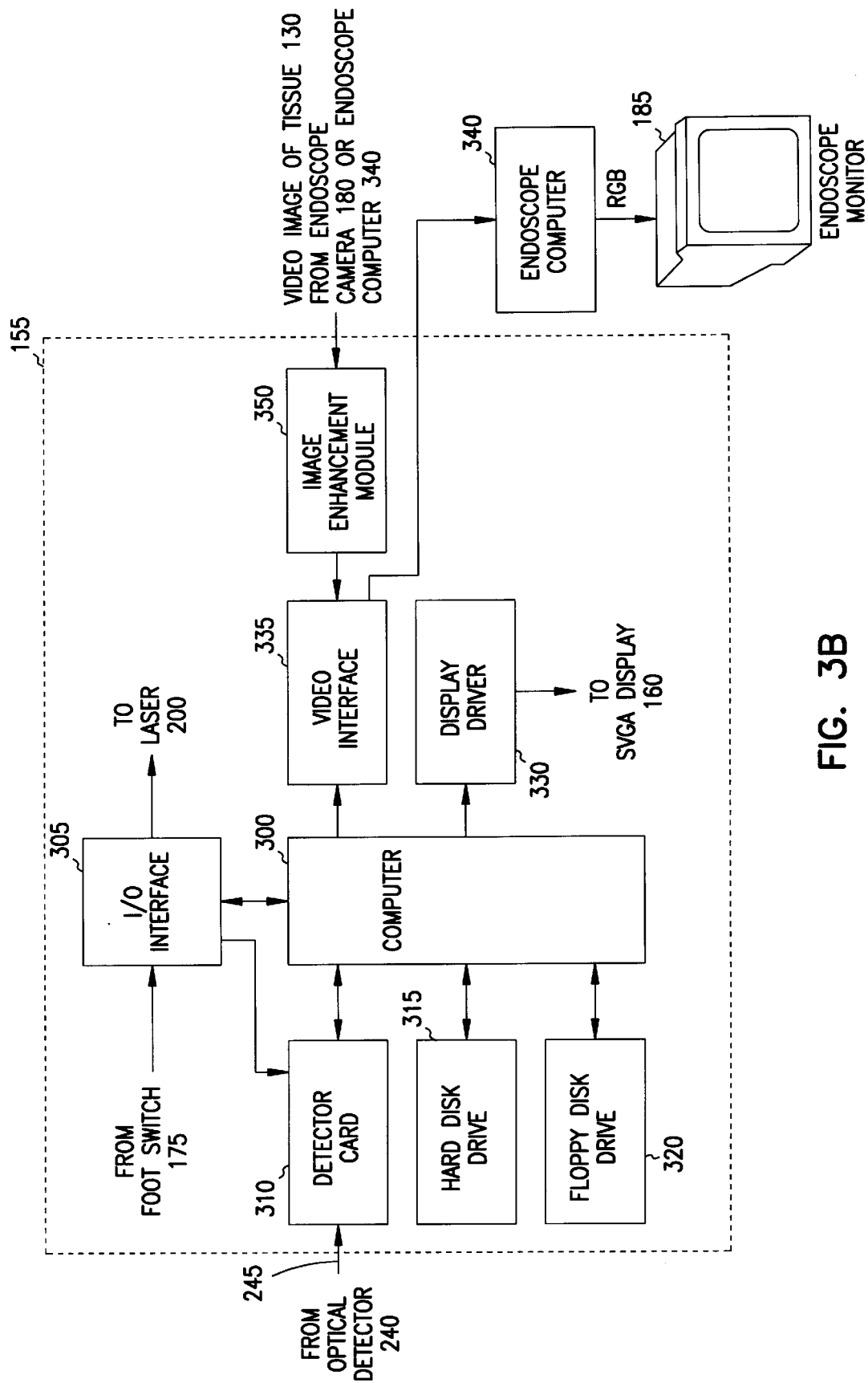
FIG. 3B is a block diagram illustrating generally another embodiment of a hardware configuration that includes image enhancement capability.

FIG. 3B is a block diagram illustrating generally another embodiment of a hardware configuration that includes an image enhancement module 350. Image enhancement module 350 performs real time color and/or contrast enhancement or other image enhancement signal processing of the endoscopic video image of the tissue 130. The image enhancement sharpens the endoscopic video image, enhances image depth, and compensates for uneven lighting. This assists the physician in locating abnormal or suspect tissue 130 sites for characterization, classification, or diagnosis using the optical biopsy techniques disclosed herein.

In one embodiment, image enhancement module 350 includes a Model CCE-3000 enhancement board from Digivision, Inc. of San Diego, Calif., which receives a video image of tissue 130 from endoscope camera 180 or endoscope computer 340. Image enhancement module 350 performs the above-described image enhancement operations, providing a resulting signal to video interface 335. In one embodiment, video interface 335 includes a real-time color lookup table for identifying and remapping particular colors in the enhanced video image. The identified colors in the video image are highlighted for the physician by video interface 335, such as by remapping the identified colors to more easily discernable colors using the look-up table of video interface 335. In this way, for example, colors that are characteristic of tissue abnormalities are recognized and highlighted for the physician. This allows the physician to easily locate such tissue sites for performing an optical biopsy using the techniques disclosed herein.

Signal Processing and Diagnostics Methods Example

Figure 4:
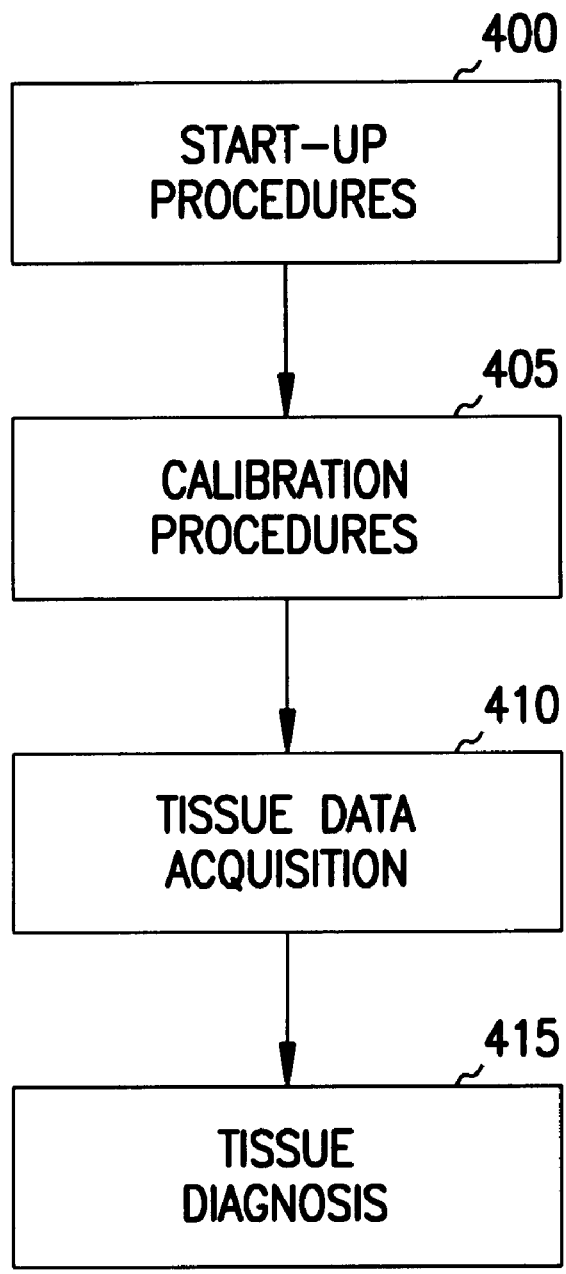
FIG. 4 is a flow chart illustrating generally an overview of one embodiment of using the present invention for characterizing or diagnosing tissue.

FIG. 4 is a flow chart illustrating generally an overview of one embodiment of using the present invention for characterizing or diagnosing tissue. As illustrated in FIG. 4, using the present invention includes performing startup procedures 400, background calibration procedures 405, tissue data acquisition 410, and tissue diagnosis 415, each of which are described in more detail below.

Startup Procedures

Figure 5:
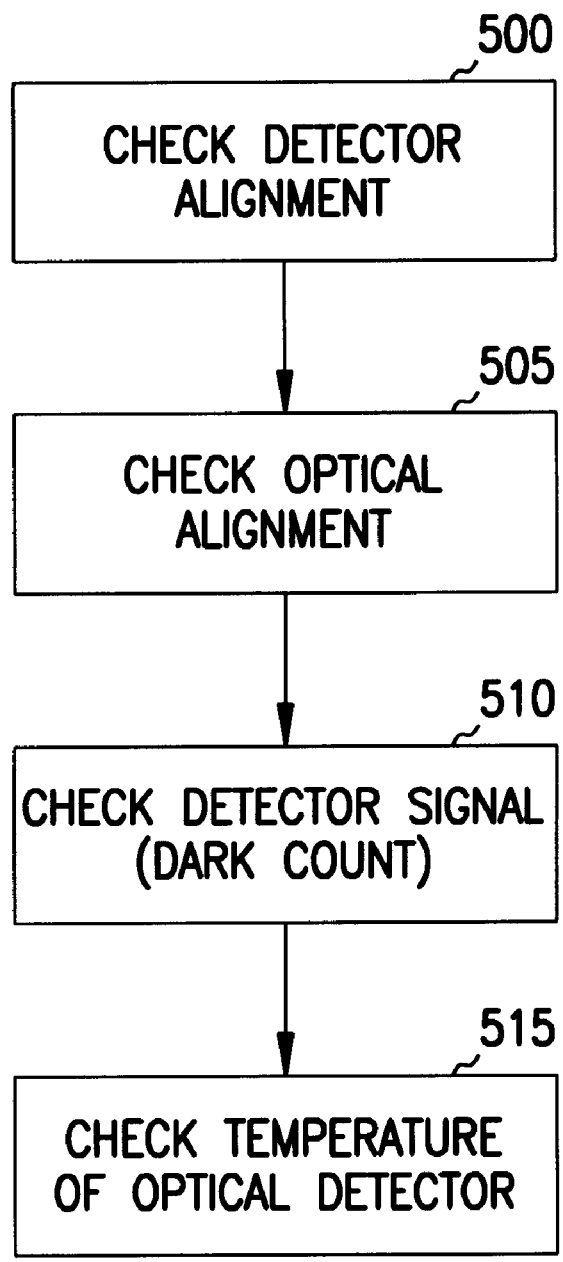
FIG. 5 is a flow chart illustrating generally one embodiment of steps included in performing startup procedures.

FIG. 5 is a flow chart illustrating generally one embodiment of steps included in performing startup procedures 400, such as when console 155 is powered on or otherwise prepared for a patient procedure. Startup procedures 400 are performed before connecting diagnostic optical fiber 135. At step 500, diode alignment of optical detector 240 is checked. This includes acquiring data from a reference material having known fluorescence characteristics. One example of a suitable reference material is barium oxide. Other reference materials may also be used during startup procedures 400. The reference material is positioned at optical coupler 220, located on console 155, at which diagnostic optical fiber 135 is later connected. A sequence of light pulses is delivered from laser 200. Resulting return light from the reference material is transmitted to and detected by optical detector 240.

Optical detector 240 and detector card 310 provide a resulting series of frames of data to computer 300, each frame of data including 1024 data bytes. Each data byte corresponds to a particular wavelength of detected return light that is obtained from one of the 1024 sets of diodes across which the return light spectra is spread. During the startup procedure 400, laser 200 delivers one light pulse for every other detection by optical detector 240. As a result, optical detector 240 performs two detections corresponding to each light pulse delivered from laser 200. A first detection corresponds to the return fluorescence in response to the light pulse. A second detection corresponds to return light detected in the absence of a light pulse delivered from laser 200 (e.g., between responses to light pulses from laser 200). The second detection provides a "dark current" measurement of the response of optical detector 240 even in the absence of light pulses from laser 200. Using the data obtained in response to light pulses from laser 200, computer 300 checks the peak intensity wavelength obtained from the set of diodes in optical detector 240. The peak intensity should be obtained from a set of diodes that is within +/−2 diode sets of a value obtained for the same reference material and earlier stored in a configuration file on computer 300.

At step 505, the optical alignment of optical detector 240 is checked. This includes checking the peak intensity magnitude of the return light obtained from the light pulses of the reference material to ensure that the peak fluorescence intensity exceeds a minimum value, for the same reference material, that was earlier stored in the configuration file. This also includes computing a percent coefficient of variation (C.V.=standard deviation÷mean×100) of the peak fluorescence intensity from the series of frames of data bytes. The coefficient of variation of the peak fluorescence intensity, over the series of data frames, should be less than a maximum value obtained for the same reference material and earlier stored in the configuration file.

At step 510, the detector signal of optical detector 240 is checked. This includes checking the signal intensity of the return light obtained in the absence of light pulses of the reference material is checked. This also includes ensuring that the peak "dark current" return light intensity is less than a maximum value that was earlier stored in the configuration file. This further includes ensuring that a "dark current" coefficient of variation, over a series of frames of dark current data, is less than a maximum value that was earlier stored in the configuration file.

At step 515, the temperature of optical detector 240 is checked to ensure that it is within a range specified in the configuration file. As described above, cooling optical detector 240 reduces its dark current noise.

Background Calibration Procedures

After startup procedures 400, diagnostic optical fiber 135 is connected to optical coupler 220 on console 155. Background calibration procedures 405 include performing a background reading to obtain a measurement of system properties. These system properties include the properties of the particular diagnostic optical fiber 135. By obtaining the background reading, a subsequent background correction can be applied to subsequent measurements characterizing tissue 130, so that the effect of these system properties can be eliminated. The background reading is performed with the distal end of diagnostic optical fiber 135 in a dark environment to provide shielding from room fluorescent lights or other light.

During the background reading, laser 200 provides a series of light pulses. Optical detector 240 detects a background return light data frame in response to each of the light pulses. In one embodiment, optical detector 240 also provides dark current data frames from corresponding detections obtained between light pulses from laser 200. Each background return light data frame is checked to ensure that its variance does not exceed a maximum value from a data frame stored in the configuration file. The background return light data frames are averaged to provide an average background data frame that is indicative of the system properties. In one embodiment, subsequent tissue characterization measurements are corrected by subtracting the average background data frame, as described below.

Alternate Background Calibration Procedures

Alternatively, background calibration procedures 405 include performing a background reading with the distal end of diagnostic optical fiber 135 aimed at a known reference material such as, for example, barium oxide. During the background reading of the reference material, laser 200 provides a series of light pulses to the reference material. Optical detector 240 detects a reference return light data frame in response to each of the light pulses. In one embodiment, optical detector 240 also provides dark current data frames from corresponding detections obtained between light pulses from laser 200. Each reference return light data frame is checked to ensure that its variance does not exceed a maximum value from a data frame stored in the configuration file. The reference return light data frames are averaged to provide an average reference data frame that is indicative of the system properties. In one embodiment, subsequent tissue characterization measurements are normalized using the average reference data frame, as described below.

Data Acquisition for Tissue Characterization

For each tissue characterization data acquisition at step 410, the temperature of optical detector 240 is checked to ensure that it is within an acceptable range specified in the configuration file. Then, laser 200 provides a series of light pulses to tissue 130. Optical detector 240 detects a return fluorescence data frame from tissue 130 in response to each of the light pulses. In one embodiment, optical detector 240 also provides dark current data frames from corresponding detections obtained between light pulses from laser 200. The acquired data frames are stored on hard disk drive 315 by computer 300 for subsequent tissue characterization and diagnosis.

Data Processing for Tissue Characterization

Figure 6:
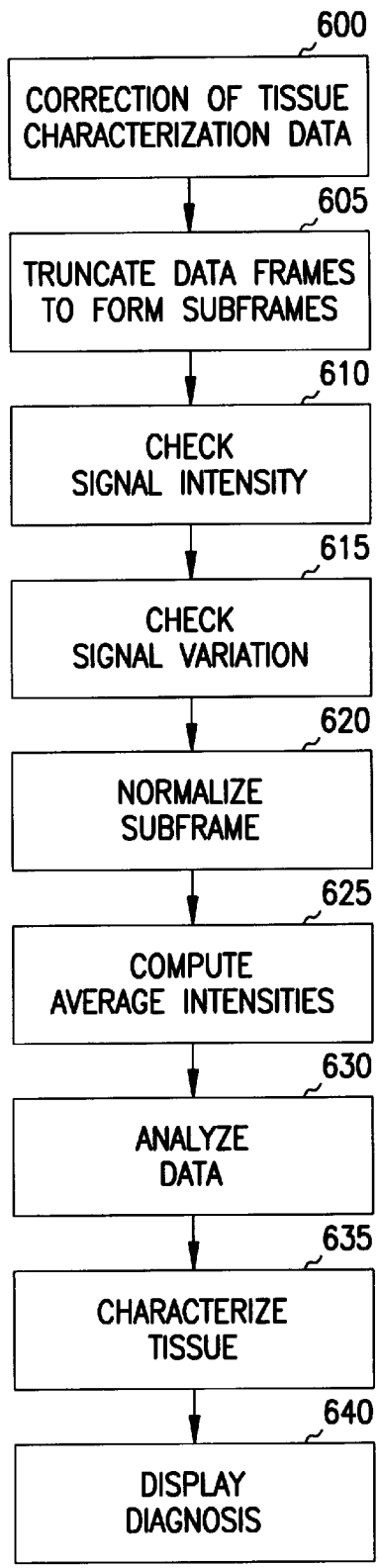
FIG. 6 is a flow chart illustrating generally one embodiment of techniques for tissue diagnosis.

FIG. 6 is a flow chart illustrating generally one embodiment of techniques for tissue diagnosis at step 415. In FIG. 6, tissue diagnosis includes correcting the tissue characterization data frames at step 600 before performing further data processing. In one embodiment, correction of the tissue characterization data frames includes subtracting the background reading provided by the average background data frame, as illustrated in Equation 1.

$$T_{ON,corrected} = K_{cal}(T_{ON} - B_{ON}) \tag{1}$$

In Equation 1, $T_{ON}$ is a return fluorescence data frame in response to an incident light pulse from laser 200 onto tissue 130, $B_{ON}$ is a return light frame in response to an incident light pulse from laser 200 into a dark environment in the absence of tissue 130, $K_{cal}$ is a calibration frame that adjusts for the individual response of each diode in optical detector 240 based on Plank's blackbody curve. $T_{ON,corrected}$ is a resulting corrected return fluorescence data frame obtained in response to an incident light pulse from laser 200 onto tissue 130. The technique illustrated in Equation 1 corrects for the system properties, including the properties of the diagnostic optical fiber 135, as described above. It does not, however, correct for the effect of endoscope light (i.e., white light provided at the distal end 110 of endoscope 100 to provide the endoscopist with a visual image of tissue 130 through viewing optics 115.

Alternatively, the tissue characterization data frames are corrected at step 600 for both system properties and endoscope light, such as illustrated in Equation 2.

$$T_{ON,corrected} = K_{cal}[(T_{ON} - T_{OFF}) - (B_{ON} - B_{OFF}0] \tag{2}$$

In Equation 2, $T_{ON}$ is a return fluorescence data frame in response to an incident light pulse from laser 200 onto tissue 130, $T_{OFF}$ is a dark current data frame from tissue 130, $B_{ON}$ is an average return light frame in response to an incident light pulse from laser 200 into a dark environment in the absence of tissue 130, $B_{OFF}$ is an average dark current data frame from a dark environment in the absence of tissue 130, and $K_{cal}$ is a calibration frame that adjusts for the individual response of each diode in optical detector 240 based on Plank's blackbody curve. $T_{ON,corrected}$ is a resulting corrected return fluorescence data frame obtained in response to an incident light pulse from laser 200 onto tissue 130.

Each frame of return fluorescence data includes 1024 data bytes, with each data byte corresponding to a distinct wavelength. For tissue characterization, only those wavelengths containing substantial return fluorescence data are of interest. In one embodiment, each frame is truncated at step 605 to form a subframe, containing only the particular wavelength range of interest, for further signal processing. In one example, the subframe corresponds to only those wavelengths that are approximately between 375 nm and 600 nm.

At step 610, the acquired signal intensity is checked. This includes checking the corrected peak intensity of each subframe to ensure that it exceeds a minimum value stored in the configuration file. Next, at step 615, the signal variation is checked. This includes forming a set of coefficients. Each coefficient corresponds to a particular wavelength in the wavelength range, and is formed from the corresponding data byte in each subframe of the series of data subframes. A comparison with corresponding values stored in the configuration file ensure that each coefficient does not exceed a maximum value for that particular wavelength of light.

At step 620, each subframe is individually normalized. In one example, the data bytes in each subframe are summed. Each data byte is then divided by the sum of the data bytes for its subframe. In another example, each data bytes in each subframe is divided by the sum of the data bytes in the average reference data frame (obtained from a reference material such as, for example, barium oxide, as described above). In a further example, each data byte in each subframe is divided by the maximum intensity data bytes of the average reference data frame obtained from the reference material. The above-listed normalization techniques are enumerated for illustrative purposes only. Other normalization techniques will be readily apparent and, alternatively, normalization could also be omitted.

At step 625, a set of average intensities is formed. Each average intensity corresponds to a particular wavelength of light in the wavelength range, and is formed from the corresponding normalized data byte in each normalized subframe of the sequence of data. As a result of step 625, a single average intensity subframe is formed from the series of subframes of data.

At step 630, the data is analyzed. In one embodiment, the data analysis includes using the average intensities, obtained at step 625, at particular wavelengths in the average intensity subframe. One embodiment of such data analysis is illustrated by way of example, but not by way of limitation, in Equation 3.

$$S = C + B_1 I_{390} + B_2 I_{425} + B_3 I_{460} + B_4 I_{500} + B_5 I_{525} \qquad (3)$$

In Equation 3, $I_{390}$, $I_{425}$, $I_{460}$, $I_{500}$, $I_{525}$ are the normalized average intensities obtained at step 625 at wavelengths of 390 nm, 425 nm, 460 nm, 500 nm, and 525 nm, respectively. The constants C, $B_1$, $B_2$, $B_3$, $B_4$, $B_5$ are coefficients that are obtained, in one embodiment, from logistics regression analysis on other tissue samples and stored in the configuration file. One example of these constants is illustrated in Table 1. S is the score obtained when Equation 3 is applied to intensity data from a particular tissue sample.

TABLE 1

Exemplary Coefficient Values for Equation 3.

| Coefficient | Coefficient Value | Standard Error |
|---|---|---|
| C | 3.68057 | 5.54655 |
| $B_1$ | $-7.351(10)^{-4}$ | $3.109(10)^{-4}$ |
| $B_2$ | $4.552(10)^{-4}$ | $8.193(10)^{-4}$ |
| $B_3$ | $1.642(10)^{-4}$ | 0.00218 |
| $B_4$ | $-0.00525$ | 0.00694 |
| $B_5$ | 0.00646 | 0.00687 |

Although Equation 3 describes the use of particular wavelengths for tissue characterization, the invention also includes the use of different wavelengths, or a different number of wavelengths (i.e., using either fewer wavelengths, or using more wavelengths). Also, instead of using the intensity at particular wavelengths, the invention also includes the use of intensities near those particular wavelengths. For example, $I_{390}$ could alternatively be formed by averaging the intensity values of several different wavelengths centered around 390 nm, and $I_{425}$ could alternatively be formed by averaging the intensity values of several different wavelengths centered around 425 nm, etc.

In one embodiment, the score, S, from Equation 3, is used to obtain a probability factor, such as illustrated in Equation 4.

$$P = \frac{e^s}{(1 + e^s)} \qquad (4)$$

In Equation 4, e is the exponential function, S is the score obtained when Equation 3 is applied to intensity data from a particular tissue sample, and P is a resulting probability factor that is used at step 635 to characterize the tissue as being normal, hyperplastic, adenomatous, or malignant. In one embodiment, for example, if P is greater than or equal to a threshold value in the configuration file, the tissue is characterized as being adenomatous or malignant. This diagnosis indicates that treatment (e.g., taking a physical tissue biopsy sample or mechanically removing at least a portion of the tissue) should be performed. An audible or visual indicator of the result of the diagnosis is displayed at step 640, such as on display 160 or on endoscope monitor 185. On the other hand, if P is less than the threshold value, the tissue is instead classified as being normal or hyperplastic. Such a diagnosis indicates that treatment (e.g., taking a physical tissue biopsy sample or mechanically removing at least a portion of the tissue) should not be performed. An indicator of this diagnosis is also displayed at step 640 to the operator, as described above. Other threshold values of P are used to further classify the tissue, such as to distinguish between adenomatous and malignant tissue, or to distinguish between normal and hyperplastic tissue.

According to one aspect of the invention, the displayed indicator clearly indicates whether the physician should treat the tissue site, without any need for further subjective evaluation of the nature of the tissue site by the physician. In one example, a binary (i.e., two-state) audible or visual indicator, such as an icon, is displayed. The binary indicator indicates whether to (1) "treat" or "biopsy," or, alternatively, (2) "not treat" or "not biopsy". A physician performs a physical biopsy sample on the characterized tissue 130 using the forceps 140 if treatment is indicated by the displayed indicator. The physician does not perform a physical biopsy sample on the characterized tissue 130 if no treatment is indicated by the displayed indicator.

Alternative Data Analysis Examples

Figure 7:
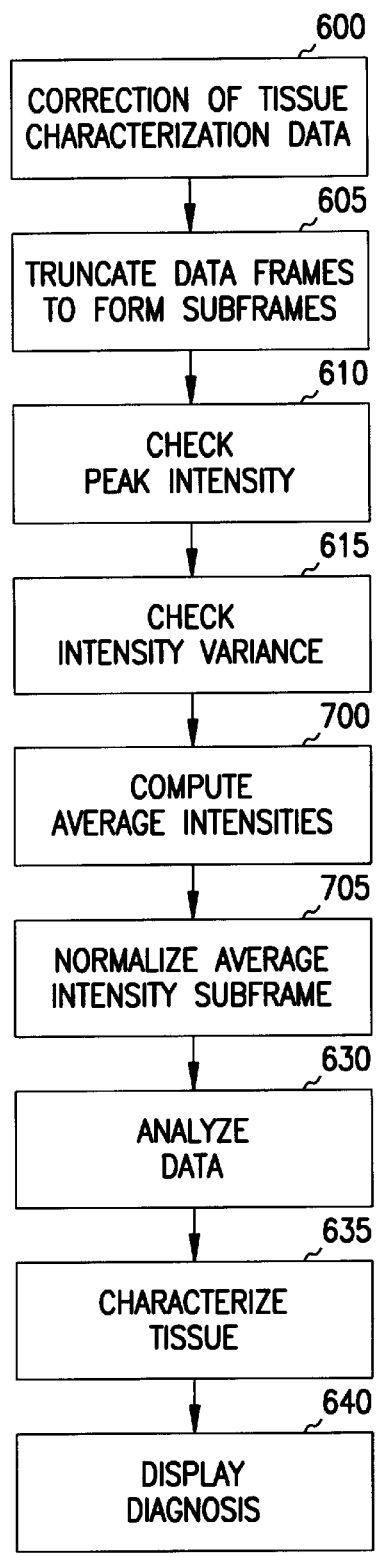
FIG. 7 is a flow chart illustrating generally an alternative embodiment of techniques for tissue diagnosis.

FIG. 7 is a flow chart illustrating generally an alternative embodiment of techniques for tissue diagnosis at step 415. At step 700, each wavelength in a subframe is averaged with the corresponding wavelengths in the other subframes, before normalization, to form a single average intensity subframe. At step 705, the average intensity subframe is then normalized by summing the data bytes in the average intensity subframe. Each data byte in the average intensity subframe is then divided by the sum of the data bytes for the average intensity subframe to provide a normalized average intensity subframe. In another alternative embodiment, normalization at step 705 is omitted, and data analysis at step 630 is performed, as described above, on the unnormalized average intensity subframe. Similarly, normalization at step 620 of FIG. 6 could also optionally be omitted.

As described above, the tissue diagnosis at step 415 uses the return fluorescence data to compute a probability that is compared to one or more previously stored threshold values to classify the tissue. The prestored threshold values used for such diagnosis comparisons are determined clinically by analyzing return fluorescence data from several histopathologically classified samples of normal, hyperplastic, adenomatous, or malignant tissue, such as by logistics regression analysis, multivariate linear regression analysis (MVLR), stepwise regression analysis, best subset analysis, spectral peak(s) ratio analysis, neural network analysis, or any other suitable data analysis technique. These data analysis techniques are also used to compute coefficient values, such as illustrated in Equation 3 and Table 1. One example of a multivariate linear regression (MVLR) analysis technique is described in Schomacker et al., "Ultraviolet Laser-Induced Fluorescence of Colonic Tissue: Basic Biology and Diagnostic Potential," *Lasers in Surgery and Medicine*, Vol. 12, pp. 63–78 (1992), which is incorporated herein by reference. One example of best subset analysis techniques is described in A. J. Miller, "Subset Selection In Regression," Chapman Hall: London (1990), p. 229, the disclosures of which is herein incorporated by reference.

Another example of analysis of the return fluorescence data at step 630 is illustrated generally in Equation 5.

$$S = C + B_1 I_{390} + B_2 I_{425} + B_3 I_{460} + B_4 I_{525} \quad (5)$$

In Equation 5, $I_{390}$, $I_{425}$, $I_{460}$, $I_{525}$ are normalized average intensities obtained at step 625 at wavelengths of 390 nm, 425 nm, 460 nm, and 525 nm, respectively. These wavelengths correspond to fluorescence variables resulting from particular components of the tissue, i.e., collagen, hemoglobin r-absorption, NADH, and FAD, respectively. The constants C, $B_1$, $B_2$, $B_3$, $B_4$, are coefficients obtained from the configuration file, one example of which is illustrated in Table 2. These coefficients are derived, for example, by the MVLR techniques carried out on other tissue samples, as described above. S is the score obtained when Equation 5 is applied to intensity data from a particular tissue sample. S is used at step 635, in comparison to one or more threshold values stored in the configuration file, to characterize the tissue as being normal, hyperplastic, adenomatous, or malignant. Such threshold values are derived, for example, by the MVLR techniques carried out on other tissue samples, as described above.

TABLE 2

Exemplary Coefficient Values for Equation 5.

| Coefficient | Coefficient Value |
| --- | --- |
| C | 1.2 |
| $B_1$ | −100 |
| $B_2$ | −2.47 |
| $B_3$ | −7.99 |
| $B_4$ | −1.52 |

Another example of analysis of the return fluorescence data at step 630 is illustrated generally in Equation 6.

$$S = C + B_1 I_{350} + B_2 I_{365} + B_3 I_{380} + B_4 I_{454} + B_5 I_{483} + B_6 I_{543} + B_7 I_{676} + B_8 I_{691} \quad (6)$$

In Equation 6, $I_{350}$, $I_{365}$, $I_{380}$, $I_{454}$, $I_{483}$, $I_{543}$, $I_{676}$, and $I_{691}$ are normalized average intensities obtained at step 625 at wavelengths of 350 nm, 385 nm, 380 nm, 454 nm, 483 nm, 543 nm, 676 nm, and 691 nm respectively. The constants C, $B_1$, $B_2$, $B_3$, $B_4$, $B_5$, $B_6$, $B_7$, and $B_8$ are coefficients obtained from the configuration file, one example of which is illustrated in Table 3. These coefficients are derived, for example, by the stepwise regression techniques carried out on other tissue samples, as described above. S is the score obtained when Equation 6 is applied to intensity data from a particular tissue sample. S is used at step 635, in comparison to one or more threshold values stored in the configuration file, to characterize the tissue (e.g., as being normal, hyperplastic, adenomatous, or malignant), such as described above. Such threshold values are derived, for example, by stepwise regression techniques carried out on other tissue samples, as described above.

TABLE 3

Exemplary Coefficient Values for Equation 6.

| Coefficient | Coefficient Value |
| --- | --- |
| C | 12.617 |
| $B_1$ | −4178 |
| $B_2$ | 2486 |
| $B_3$ | −724 |
| $B_4$ | −1460 |
| $B_5$ | 679 |
| $B_6$ | −2008 |
| $B_7$ | −3380 |
| $B_8$ | 4421 |

Figure 8:
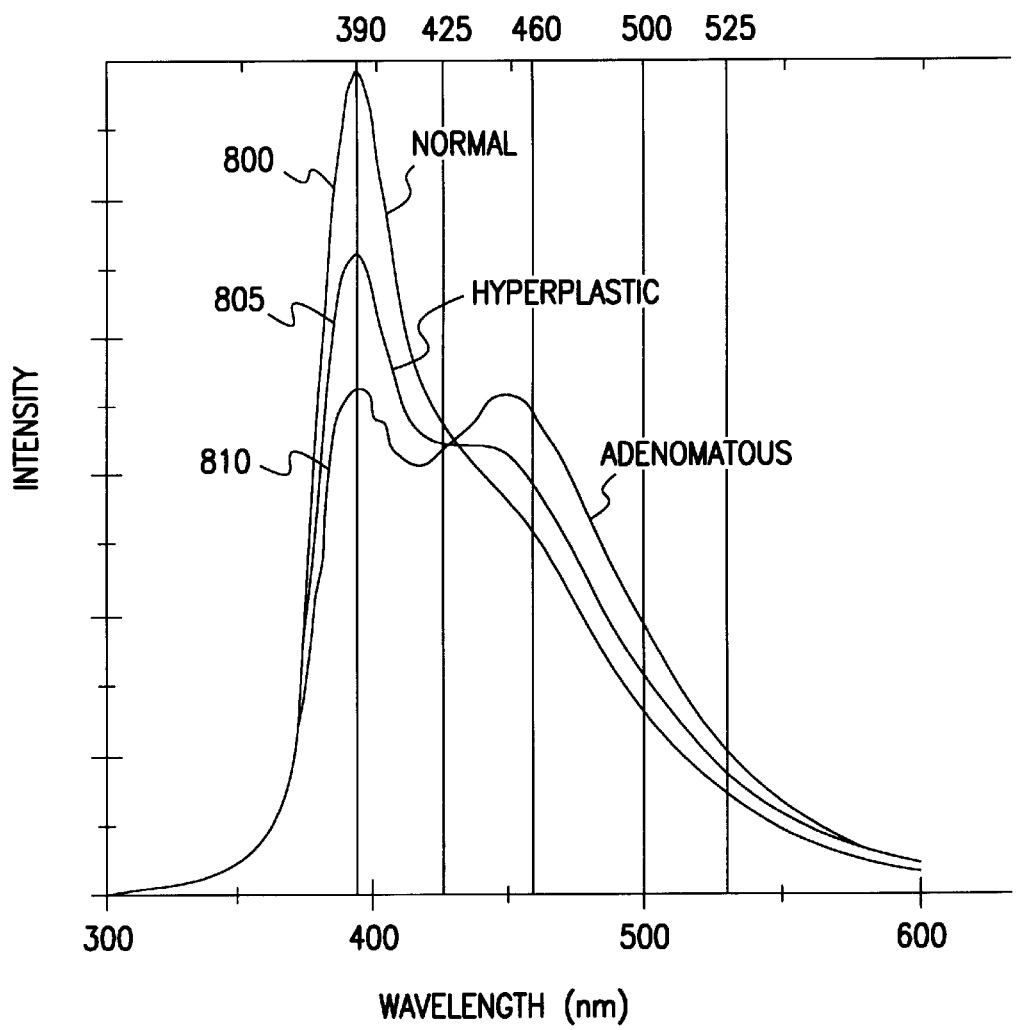
FIG. 8 is a graph illustrating generally intensity vs. wavelength from colonic tissue that is normal, hyperplastic, and adenomatous.

Another data analysis technique includes evaluation of shape of an intensity vs. wavelength curve such as, for example, the curve provided by the average intensity subframe at step 625. FIG. 8 is a graph illustrating generally intensity vs. wavelength for wavelengths between 300 nm and 600 nm from colonic tissue 130 that is normal, as illustrated by curve 800, hyperplastic, as illustrated by curve 805, and adenomatous, as illustrated by curve 810. FIG. 8 also illustrates, by way of example, the particular sample wavelengths (e.g., 390 nm, 425 nm, 460 nm, 500 nm, and 525 nm) used in the example of Equation 3.

One curve-shape evaluation technique includes evaluating the slope of the intensity vs. wavelength curve at various sample wavelengths, such as those illustrated in Equation 3 and FIG. 8. For example, a difference is taken between the intensities at 390 nm and a substantially adjacent wavelength to provide an indication of the slope of the intensity vs. wavelength curve at that particular wavelength. Alternatively, multiple differences at approximately adjacent wavelengths is taken and averaged to provide an indication of slope. Similar slope information is obtained at other wavelengths, such as 425 nm, 460 nm, 500 nm, and 525 nm. The slope information is used, either alone, or in combination with intensity (magnitude) information, to characterize the tissue.

In one embodiment, this slope information is used to provide tissue characterization and diagnosis in place of the other data analysis techniques of step 630. In another embodiment, the slope information provides an adjunctive diagnosis in addition to the data analysis technique of step 630. In addition to slope information, curve-shaping evaluation also includes similarly evaluating curvature of the intensity vs. wavelength data, or any other suitable curve-shape evaluation technique.

Another example of analysis of the return fluorescence data at step 630 is illustrated generally in Equation 7.

$$X = C_1(S_{435.4}) + C_2(S_{467.4}) \quad (7)$$

In Equation 7, $S_{435.4}$ and $S_{467.4}$ are slopes of the intensity vs. wavelength curve centered around example wavelengths of approximately 435.4 nm and 467.4 nm, respectively, and $C_1$ and $C_2$ are coefficients stored in the configuration file, one example of which is illustrated in Table 4. These coefficients are derived, for example, by the best subset analysis techniques carried out on other tissue samples, as described above. X is score obtained when Equation 7 is applied to intensity data obtained from a particular tissue sample. X is used at step 635, in comparison to one or more threshold values stored in the configuration file, to characterize the tissue as being normal, hyperplastic, adenomatous, or malignant, such as described above. Such threshold values are derived, for example, by best subset analysis carried out on other tissue samples, as described above.

TABLE 4

Example Coefficient Values for Equation 7.

| Coefficient | Coefficient Value | Standard Error |
|---|---|---|
| $C_1$ | 24.14 | 2.117 |
| $C_2$ | −23.47 | 6.058 |

As described above, many different techniques can be used to form slopes $S_{4354}$ and $S_{4674}$. One embodiment, for example, uses normalized intensities from 11 adjacent diodes in optical detector 240, the 11 adjacent diodes centered around a center wavelength (e.g., 435.4 nm). Differences are extracted from the intensities obtained from diodes at adjacent detected wavelengths. The resulting differences are averaged to obtain an average slope at the center wavelength (e.g., at 435.4 nm).

Another example of analysis of the return fluorescence data at step 630 is illustrated generally in Equation 8, which includes analysis of both slope and intensity data for characterizing tissue.

$$X = C_1(S_{383.3}) + C_2(I_{409.3}) + C_3(S_{468.6}) \quad (8)$$

In Equation 8, $S_{383.3}$ and $S_{468.6}$ are slopes of the intensity vs. wavelength curve centered around example wavelengths of approximately 383.3 nm and 468.6 nm, respectively, $I_{409.3}$ is an intensity value at a wavelength of approximately 409.3 nm, and $C_1$, $C_2$, and $C_3$ are coefficients stored in the configuration file, one example of which is illustrated in Table 5. These coefficients are derived, for example, by best subset analysis techniques carried out on other tissue samples, as described above. X is the score obtained Equation 8 is applied to intensities obtained from a particular tissue sample. X is used at step 635, in comparison to one or more threshold values stored in the configuration file, to characterize the tissue as being normal, hyperplastic, adenomatous, or malignant, such as described above. Such threshold values are derived, for example, by best subset analysis techniques carried out on other tissue samples, as described above.

TABLE 5

Example Coefficient Values for Equation 8.

| Coefficient | Coefficient Value | Standard Error |
|---|---|---|
| $C_1$ | 5.272 | 1.1000 |
| $C_2$ | −0.6965 | 0.06125 |
| $C_3$ | −41.62 | 5.831 |

Patient Flow Chart

Figure 9:
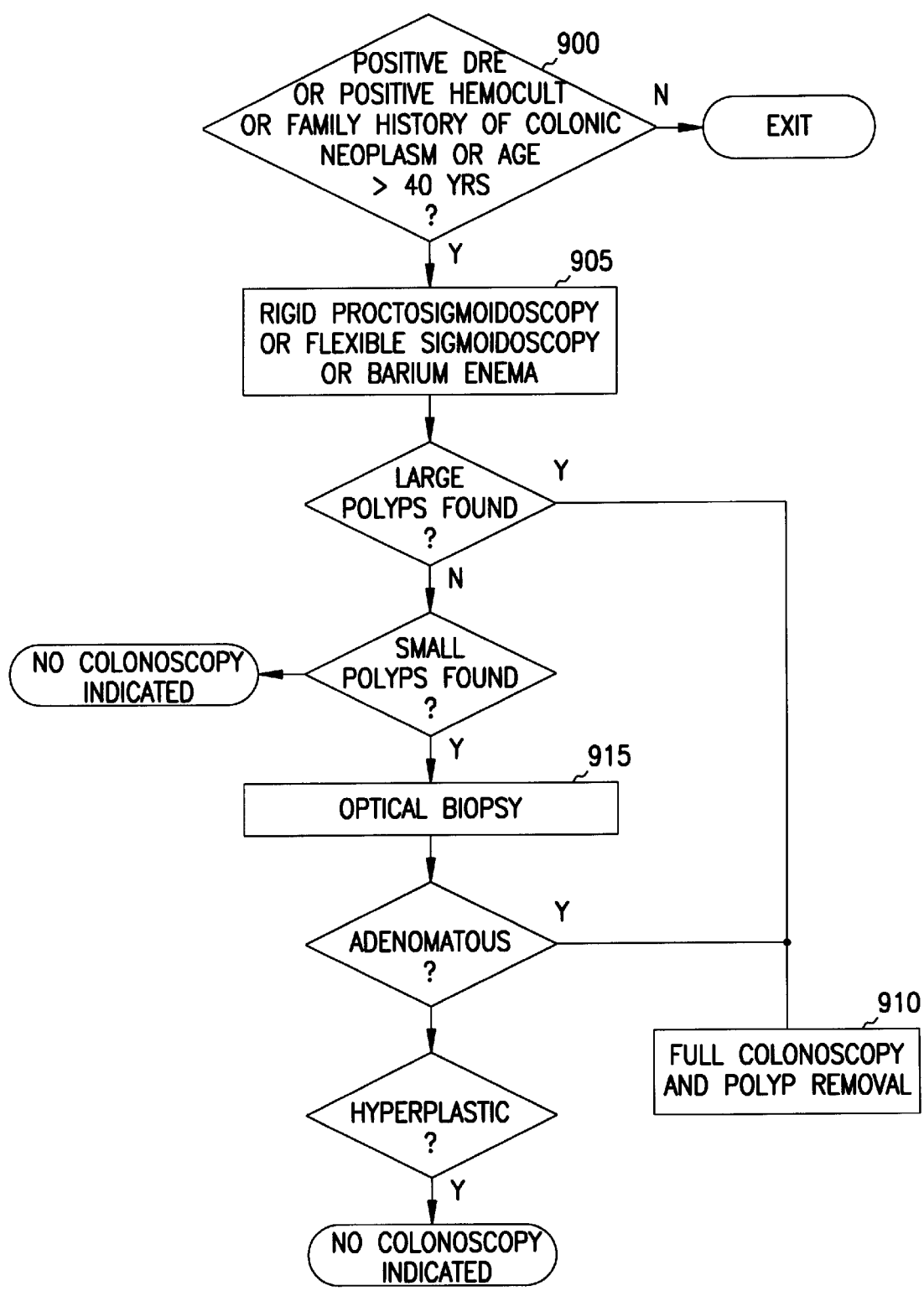
FIG. 9 is a flow chart illustrating generally one method of diagnosing patients with lower gastrointestinal symptoms.

FIG. 9 is a flow chart illustrating generally, by way of example, but not by way of limitation, one method of diagnosing patients with lower gastrointestinal (e.g., colonic) symptoms. At step 900, a physician performs a first preliminary screening, the results of which may indicate a need for further investigation. For example, a digital rectal exam (DRE), in which the physician feels the interior of the patient's lower colon, may indicate that polyps or other tissue abnormalities are present. In another example, a patient may have a positive hemocult (i.e., blood in the patient's stools), which also indicates the possibility of tissue abnormalities. Other indicators for further investigation include a family history of colonic neoplasm, or even the age of the patient (e.g., greater than 40 years) may indicate that further investigation is warranted.

At step 905, a second preliminary screening is performed. For example, such procedures might include a subjective visual inspection of the interior of the colon using proctosigmoidoscopy or flexible sigmoidoscopy devices. In another example, such procedures might include introducing a barium enema into the patient's lower colon and a subsequent subjective radiological evaluation for tissue abnormalities.

If large polyps are found as a result of the secondary preliminary screening of step 905, then, at step 910, an entire-length colonoscopy is performed, and the large polyps are removed. For example, a polypectomy may involve removing the large polyps using a forceps, needle, snare or other mechanical device operating as an endoscopic accessory. In another example, electrosurgical techniques are used to fulgurate the polyps. At step 910, the entire-length colonoscopy includes a complete examination of the colon for the presence of synchronously occurring polyps in the proximal colon.

If small polyps are found as a result of the secondary preliminary screening at step 905, then, at step 915, an optical biopsy is performed to characterize the tissue 130 according to the above-described techniques (e.g., see FIGS. 4–7) of the present invention. Individual tissue 130 sites are illuminated and characterized as either normal, hyperplastic, adenomatous, or malignant. If the tissue 130 sites are either adenomatous or malignant, full colonoscopy is performed, as described above, at step 910. If the tissue 130 sites are either normal or hyperplastic, no colonoscopy is indicated.

Alternatively, as described above, a physical biopsy sample is taken and histopathologically analyzed if the optical biopsy indicates adenomatous or malignant tissue 130, and then colonoscopy is performed at step 910. However, the physical biopsy and histopathological analysis is optional and is not essential to practice other aspects of the present invention.

Tissue characterization according to the present invention eliminates the need for a subjective visual evaluation of the tissue by the physician. It is histopathologically estimated that between 50% and 60% of small (less than 5 mm in diameter) polyps are adenomatous. Recently endoscopic studies, however, indicate that it is difficult or virtually impossible to subjectively visually differentiate between small hyperplastic and adenomatous polyps.

Since the present invention provides virtually real-time tissue diagnosis, accurate characterization is possible even if many polyps or other tissue abnormalities are present. Furthermore, the optical biopsy at step 915 can also be performed earlier in the patient flow chart of FIG. 9, such as during the flexible sigmoidoscopy of step 905. Furthermore, a physical biopsy sample could also be taken at step 905 based on the above-described optical biopsy characterization of the tissue.

The optical biopsy of the present invention is also useful during follow-up procedures to the colonoscopy and polyp removal of step 910. During the follow-up, tissue characterization by optical biopsy indicates whether the polyp resection was complete.

Other Applications

Though a particular embodiment of the invention is described above with respect to characterizing gastrointestinal tissue, it is understood that the techniques of the present invention find application in many other fields of medicine including, but not limited to: cardiovascular, urological, pulmonary, reproductive, dermatology, surgery, and general medicine. Moreover, the tissue characterization and treatment described above applies not only to polyp diagnosis and removal of physical biopsy samples, but also applies to characterization of smaller malignancies located in surrounding tissue, and characterization of healthy perimeter tissue surrounding abnormal tissue sites.

Particular aspects of the invention are described above with respect to light-induced fluorescence. Aspects of the invention are also capable of use with other tissue characterization techniques including, but not limited to: optical coherent tomography, interference and attenuation across a spectrum (interferometry), optical-acoustic and/or acoustic-optical imaging, fluorescence imaging, photomigration techniques, time-resolved fluorescence spectroscopy, frequency-domain fluorescence spectroscopy, reflection/absorption spectroscopy (elastic scattering), Rayleigh scattering, Raman scattering, and other linear or nonlinear optical techniques. For example, in one embodiment of the invention, providing a tissue diagnosis is on spectroscopic analysis of return fluorescence intensities in combination with one of the above-listed other tissue characterization techniques.

Extrinsic fluorescence-enhancing agents, for enhancing a fluorescence image of the tissue, are not required to practice the present invention, however, the present invention is capable of use with such contrast agents. Moreover, aspects of the invention are also capable of use with other extrinsic agents, such as genetic markers, for the detection of cancer and other tissue abnormalities.

Particular aspects of the present invention have been described with respect to a single optical fiber for diagnosing the tissue, allowing easy integration with a tissue treatment device. However, aspects of the present invention are also capable of use with multiple fibers for transmitting or collecting electromagnetic energy for diagnosing the tissue.

The techniques disclosed are not limited to tissue characterization and treatment, but could also be applied to characterizing other substances using minimally invasive laparoscopic or general surgical guidance techniques to avoid the complications of damage to surrounding healthy structures. For example, the above-described system could also be used to differentiate between oxygenated and deoxygenated hemoglobin, such as for in situ differentiation between arteries and veins using minimally invasive techniques. Many other embodiments will be apparent to those of skill in the art upon reviewing the above description.

CONCLUSION

The present invention provides, among other things, systems, devices and methods for using native fluorescence to characterize tissue without requiring fluorescence-enhancing agents. Image enhancement capability allows easy location of tissue sites to be diagnosed. The system allows the use of a single diagnostic optical fiber that is coaxially integrated with a treatment apparatus. Immediate diagnosis allows immediate treatment, such as by using the integrated diagnostic and treatment apparatus. As a result, treatment does not require removing a diagnostic apparatus, and trying to relocate the tissue site using a treatment apparatus. The present invention also allows easy integration with existing endoscopy equipment, including endoscopes and/or laparoscopes, endoscope monitors, and endoscope computers.

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A method comprising:

introducing into a living organism an endoscope having viewing optics and a conduit;

introducing a diagnostic optical fiber through the conduit into proximity with tissue at a distal end of the endoscope;

transmitting excitation electromagnetic energy through the diagnostic optical fiber to the tissue without requiring fluorescence-enhancing agents;

receiving an electromagnetic energy signal through the diagnostic optical fiber from the tissue in response to the excitation electromagnetic energy;

providing a diagnosis of the tissue using an analysis of a signal that is based on forming an intensity spectrum of the received electromagnetic energy; and treating the tissue, if indicated by the diagnosis, while the diagnostic optical fiber is still in the conduit of the endoscope, wherein treating the tissue consists essentially of at least one of: taking a physical biopsy sample of at least a portion of the tissue, mechanically removing at least a portion of the tissue, performing electrosurgery on at least a portion of the tissue, delivering a drug or other chemical agent to at least a portion of the tissue, and providing photodynamic therapy to at least a portion of the tissue.

2. The method of claim 1, in which providing a diagnosis of the tissue includes:
   computing a diagnosis probability based on intensities at particular wavelengths in the intensity spectrum; and
   comparing the diagnosis probability to a threshold probability to characterize the tissue.

3. The method of claim 2, in which comparing the diagnosis probability to a threshold probability includes basing at least one of the diagnosis probability and the threshold probability on a stepwise discriminate analysis of data obtained from other tissue samples.

4. The method of claim 2, in which comparing the diagnosis probability to a threshold probability includes basing at least one of the diagnosis probability and the threshold probability on a logistics regression analysis of data obtained from other tissue samples.

5. The method of claim 2, in which comparing the diagnosis probability to a threshold probability includes basing at least one of the diagnosis probability and the threshold probability on a best subset analysis of data obtained from other tissue samples.

6. The method of claim 2, further comprising providing an audio or visual indicator of the diagnosis.

7. The method of claim 6, in which providing an indicator of the diagnosis includes displaying an intensity vs. wavelength graph.

8. The method of claim 6, in which providing an indicator of the diagnosis includes displaying an icon that indicates whether treatment of the tissue is indicated.

9. The method of claim 6, in which providing an indicator includes displaying the indicator overlaying a visual image of the tissue displayed on an endoscope monitor.

10. The method of claim 2, further comprising normalizing the intensity spectrum to a reference intensity spectrum by dividing each intensity at a particular wavelength in the intensity spectrum by an intensity at the corresponding wavelength in the reference intensity spectrum.

11. The method of claim 2, further comprising normalizing the intensity spectrum by dividing each intensity at a particular wavelength in the intensity spectrum by a sum of intensities over a range of wavelengths in the intensity spectrum.

12. The method of claim 2, further comprising correcting the intensity spectrum by subtracting a background reading.

13. The method of claim 12, further comprising normalizing the intensity spectrum to a reference intensity spectrum by dividing each intensity at a particular wavelength in the intensity spectrum by an intensity at the corresponding wavelength in the reference intensity spectrum.

14. The method of claim 12, further comprising normalizing the intensity spectrum by dividing each intensity at a particular wavelength in the intensity spectrum by a sum of intensities over a range of wavelengths in the intensity spectrum.

15. The method of claim 12, in which subtracting a background reading includes correcting for endoscope light.

16. The method of claim 15, further comprising normalizing the intensity spectrum to a reference intensity spectrum by dividing each intensity at a particular wavelength in the intensity spectrum by an intensity at the corresponding wavelength in the reference intensity spectrum.

17. The method of claim 15, further comprising normalizing the intensity spectrum by dividing each intensity at a particular wavelength in the intensity spectrum by a sum of intensities over a range of wavelengths in the intensity spectrum.

18. The method of claim 2, in which providing the diagnosis of the tissue includes forming the diagnosis based on a slope of the intensity spectrum at particular wavelengths.

19. The method of claim 18, in which providing the diagnosis of the tissue includes forming the diagnosis based on a curvature of the intensity spectrum at particular wavelengths.

20. The method of claim 2, in which providing a diagnosis of the tissue further comprises also basing the diagnosis of the tissue on at least one of: optical coherent tomography, interferometry, optical-acoustic imaging, acoustic-optical imaging, fluorescence imaging, photomigration, time-resolved fluorescence spectroscopy, frequency-domain fluorescence spectroscopy, elastic scattering, Rayleigh scattering, and Raman scattering.

21. The method of claim 1, in which transmitting excitation electromagnetic energy includes voice-activating a light source for diagnosing the tissue.

22. The method of claim 1, in which providing a diagnosis of the tissue includes:
   forming a probability factor P according to the equation $P=e^S/(1+e^S)$, wherein:
   $$s = C + \sum_{i=1}^{n} B_i \cdot I_i$$
   and C is a constant, I is a detected return fluorescence intensity at a particular wavelength, B is a constant corresponding to the particular wavelength, and n is any positive integer; and
   comparing the probability factor P to a predetermined value to diagnose the tissue.

23. The method of claim 22, in which C, B, and P are based on a logistics regression analysis of data obtained from other tissue samples.

24. The method of claim 1, in which providing a diagnosis of the tissue includes:
   forming a score S, wherein:
   $$s = C + \sum_{i=1}^{n} B_i \cdot I_i$$
   and C is a constant, I is a detected return fluorescence intensity at a particular wavelength, B is a constant corresponding to the particular wavelength, and n is any positive integer; and
   comparing the score S to a predetermined threshold value to diagnose the tissue.

25. The method of claim 24, in which at least one of C, B, and the predetermined threshold value are based on at least one of: logistics regression analysis, multivariate linear regression (MVLR) analysis, stepwise regression analysis, best subset analysis, spectral peak(s) ratio analysis, and neural network analysis.

26. The method of claim 1, in which providing a diagnosis of the tissue includes:
   forming a score X, wherein:
   $$X = \sum_{i=1}^{n} C_i \cdot S_i$$
   and C is a constant corresponding to the particular wavelength, S is a slope of the detected return fluorescence intensity spectrum at a particular wavelength, and n is any positive integer; and
   comparing the score X to a predetermined threshold value to diagnose the tissue.

27. The method of claim 26, in which at least one of C and the predetermined threshold value are based on at least one of: logistics regression analysis, multivariate linear regression (MVLR) analysis, stepwise regression analysis, best subset analysis, spectral peak(s) ratio analysis, and neural network analysis.

28. The method of claim 1, in which providing a diagnosis of the tissue includes:
forming a score X, wherein:

$$X = \sum_{i=1}^{m} C_i \cdot S_i + \sum_{j=1}^{n} C_j \cdot I_j$$

and C is a constant corresponding to the particular wavelength, S is a slope of the detected return fluorescence intensity spectrum at a particular wavelength, I is an intensity of the detected return fluorescence at a particular wavelength, and m and n are positive integers; and
comparing the score X to a predetermined threshold value to diagnose the tissue.

29. The method of claim 28, in which at least one of C and the predetermined threshold value are based on at least one of: logistics regression analysis, multivariate linear regression (MVLR) analysis, stepwise regression analysis, best subset analysis, spectral peak(s) ratio analysis, and neural network analysis.

30. A method comprising:
introducing into a living organism an endoscope having viewing optics and a conduit;
displaying, on an endoscope monitor, a view at a distal end of the endoscope;
introducing a diagnostic optical fiber through the conduit into proximity with tissue at the distal end of the endoscope;
transmitting excitation electromagnetic energy through the diagnostic optical fiber to the tissue;
receiving electromagnetic energy through the diagnostic optical fiber from the tissue in response to the excitation electromagnetic energy;
providing a diagnosis of the tissue using an analysis of a signal that is based on forming an intensity spectrum of the received electromagnetic energy; and
displaying an indicator of the diagnosis and a visual image of the tissue endoscope monitor.

31. The method of claim 30, in which displaying an indicator of the diagnosis includes displaying an intensity vs. wavelength graph.

32. The method of claim 30, in which displaying an indicator of the diagnosis includes displaying an icon that indicates whether treatment of the tissue is indicated.

33. A method comprising:
introducing into a living organism an endoscope having viewing optics and a conduit;
introducing a diagnostic optical fiber through the conduit into proximity with tissue at a distal end of the endoscope;
obtaining a video image of the tissue;
digitally enhancing the video image of the tissue;
locating a tissue site based on the enhanced video image of the tissue;
transmitting excitation electromagnetic energy through the diagnostic optical fiber to the located tissue site without requiring fluorescence-enhancing agents;
receiving electromagnetic energy through the diagnostic optical fiber from the tissue site in response to the excitation electromagnetic energy;
providing a diagnosis of the tissue site using an analysis of a signal that is based on forming an intensity spectrum of the received electromagnetic energy; and
treating the tissue site, if indicated by the diagnosis, while the diagnostic optical fiber is still in the conduit of the endoscope, wherein treating the tissue site consists essentially of at least one of: taking a physical biopsy sample of at least a portion of the tissue site, mechanically removing at least a portion of the tissue site, performing electrosurgery on at least a portion of the tissue site, delivering a drug or other chemical agent to at least a portion of the tissue site, and providing photodynamic therapy to at least a portion of the tissue site.

34. A method comprising:
introducing into a patient's gastrointestinal tract an endoscope having viewing optics and a working channel conduit;
introducing a diagnostic optical fiber and coaxially integrated forceps through the conduit into proximity with tissue at a distal end of the endoscope;
generating excitation laser light pulses;
coupling the excitation laser light pulses to the diagnostic optical fiber using a dichroic mirror;
transmitting excitation laser light pulses through the diagnostic fiber to the tissue without requiring fluorescence-enhancing agents;
receiving return light through the diagnostic optical fiber from the tissue in response to the excitation laser light pulses;
filtering to obtain a return fluorescence light by removing components of the return light having a wavelength that is approximately shorter than approximately 355 nanometers;
spatially separating the filtered return light to obtain a return fluorescence spectrum;
detecting the intensity of the return fluorescence spectrum at a plurality of wavelengths;
correcting the detected return fluorescence intensity spectrum by subtracting a background reading including an endoscope light correction;
characterizing the tissue, which includes:
forming a probability factor P according to the equation $P = e^S/(1+e^S)$, wherein:

$$s = C + \sum_{i=1}^{n} B_i \cdot I_i$$

and C is a constant, I is a detected return fluorescence intensity at a particular wavelength, and B is a constant corresponding to the particular wavelength; and
comparing the probability factor P to a predetermined value to diagnose the tissue;
displaying an indicator of the diagnosis on an endoscope monitor, together with a visual image of the tissue; and
taking a physical biopsy sample of the tissue, if indicated by the diagnosis, while the diagnostic optical fiber is still in the conduit of the endoscope.

35. An endoscopic system for analyzing, diagnosing, and treating tissue, the system comprising:

an electromagnetic excitation energy source;

a single diagnostic optical fiber, adapted to extend through a conduit in an endoscope, from a proximal end of the endoscope to a distal end of the endoscope, for transmitting the electromagnetic excitation energy to a tissue and receiving an electromagnetic response from the tissue at the distal end of the endoscope;

a spectrophotometer, receiving the electromagnetic response and providing a resulting spectral response signal;

an optical coupler, coupling the electromagnetic excitation energy from the energy source to the diagnostic optical fiber, and coupling the electromagnetic response to the spectrophotometer;

a diagnosis module, receiving the spectral response signal and providing a resulting tissue classification without requiring fluorescence-enhancing agents at the tissue; and a tissue treatment apparatus that is integrally formed with the diagnostic optical fiber, wherein the tissue treatment apparatus is selected from the group consisting essentially of a biopsy forceps, a biopsy needle, polyp snare, an radio-frequency (RF) ablation apparatus, an electrosurgical apparatus, a drug or chemical agent delivery apparatus, a photodynamic therapy (PDT) apparatus, and a guidewire catheter.

36. The system of claim 35, in which the optical coupler includes:

a mirror for reflectively coupling the electromagnetic excitation energy to the diagnostic optical fiber; and at least one lens for coupling the electromagnetic response to the spectrophotometer.

37. The system of claim 36, further comprising an interface circuit, adapted for displaying an indicator of at least one of the spectral response signal and the tissue classification to an endoscope monitor.

38. The system of claim 35, in which the tissue treatment apparatus is coaxially formed with the single diagnosing optical fiber concentrically located at the center of the tissue treatment apparatus.

39. The system of claim 35, in which the electromagnetic excitation energy source is coupled to and actuated by a switch that is located on the endoscope.

40. The system of claim 35, in which the electromagnetic excitation energy source is voice-actuated.

41. The system of claim 35, further comprising an interface circuit for receiving a video signal image of the tissue at the distal end of the endoscope, and adapted for providing the video signal image together with an indicator of the tissue classification to an endoscope monitor, the interface circuit being coupled to the diagnosis module.

42. The system of claim 41, further comprising an image enhancement module, coupled to the interface circuit, for enhancing the video signal image of the tissue at the distal end of the endoscope.

43. An endoscopic system for analyzing, diagnosing, and treating tissue, the system comprising:

a pulsed laser providing electromagnetic excitation energy;

a single diagnostic optical fiber, adapted to extend through a working channel conduit in an endoscope, from a proximal end of the endoscope to a distal end of the endoscope, for transmitting the electromagnetic excitation energy to and receiving an electromagnetic response from a colonic tissue site at the distal end of the endoscope, wherein the single diagnostic fiber is coaxially and concentrically integrally formed within a treatment device that is selected from a group consisting essentially of at least one of: a biopsy forceps, a biopsy needle, a polyp snare, an radio-frequency (RF) ablation apparatus, an electrosurgical apparatus, a photodynamic therapy (PDT) apparatus, a drug or chemical agent delivery apparatus, a guidewire, and a catheter;

a spectrophotometer, receiving the electromagnetic response and providing a resulting spectral response signal, the spectrophotometer including:

a spectrograph for providing spatial dispersion of the spectral response signal;

an optical detector for detecting the spatially dispersed spectral response signal; and a thermoelectric cooler for regulating the temperature of the optical detector;

an optical coupler, coupling the electromagnetic excitation energy from the pulsed laser to the diagnostic optical fiber, and coupling the electromagnetic response to the spectrophotometer, the optical coupler including:

a dichroic mirror for reflectively coupling the electromagnetic excitation energy to the diagnostic optical fiber; and at least one lens for coupling the electromagnetic response to the spectrophotometer; and a diagnosis module, receiving the spectral response signal and providing a resulting tissue classification without requiring fluorescence-enhancing agents at the tissue, the diagnosis module including an executable sequence of instructions for classifying the tissue; and an interface circuit for receiving a video signal image of the tissue at the distal end of the endoscope, and adapted for providing the video signal image together with an indicator of the tissue classification to an endoscope monitor, the interface circuit being coupled to the diagnosis module.

44. The system of claim 43, further comprising an image enhancement module, coupled to the interface circuit, for enhancing the video signal image of the tissue at the distal end of the endoscope.

45. An endoscopic system for analyzing, diagnosing, and treating tissue, the system comprising:

an noncoherent electromagnetic energy source coupled to a distal end of an endoscope for illuminating tissue;

a single diagnostic optical fiber, adapted to extend through a conduit in an endoscope, from a proximal end of the endoscope to a distal end of the endoscope, for receiving an electromagnetic response from the tissue at the distal end of the endoscope;

a spectrophotometer, receiving the electromagnetic response and providing a resulting spectral response signal;

a diagnosis module, receiving the spectral response signal and providing a resulting tissue classification without requiring fluorescence-enhancing agents at the tissue; and a tissue treatment apparatus that is integrally formed with the diagnostic optical fiber, wherein the tissue treatment apparatus is selected from the group consisting essentially of at least one of: a biopsy forceps, a biopsy needle, polyp snare, an radio-frequency (RF) ablation apparatus, an electrosurgical apparatus, a drug or chemical agent delivery apparatus, a photodynamic therapy (PDT) apparatus, a guidewire, and a catheter.

* * * * *

UNITED STATES PATENT AND TRADEMARK OFFICE
CERTIFICATE OF CORRECTION

PATENT NO. : 6,174,291 B1
DATED : January 16, 2001
INVENTOR(S) : Brian T. McMahon et al.

It is certified that error appears in the above-identified patent and that said Letters Patent is hereby corrected as shown below:

Title page,
In the Inventors, delete "Brain T. McMahon" and insert -- Brian T. McMahon --, therefor.
Delete "Taylor Falls" and insert -- Taylors Falls --, therefor.

Column 14,
Line 3, delete "have" and insert -- having --, therefor.
Line 23, delete "is".

Column 16,
Line 16, delete "discemable" and insert -- discernable --, therefor.

Column 17,
Line 24, delete "is checked".

Column 18,
Line 65, delete "($B_{ON}$-$B_{OFF}$0]" and insert -- ($B_{ON}$-$B_{OFF}$)] --, therefor.

Column 19,
Line 36, delete "bytes" and insert -- byte --, therefor.

UNITED STATES PATENT AND TRADEMARK OFFICE
CERTIFICATE OF CORRECTION

PATENT NO. : 6,174,291 B1
DATED : January 16, 2001
INVENTOR(S) : Brian T. McMahon et al.

It is certified that error appears in the above-identified patent and that said Letters Patent is hereby corrected as shown below:

Column 23,
Line 44, delete "$S_{4354}$ and $S_{4674}$" and insert -- $S_{435.4}$ and $S_{467.4}$ --, therefor.
Line 67, insert -- when -- after "obtained".

Column 29,
Line 47, insert -- on the same -- after "tissue".

Signed and Sealed this

Twenty-first Day of August, 2001

*Attest:*

*Attesting Officer*

NICHOLAS P. GODICI
*Acting Director of the United States Patent and Trademark Office*